United States Patent
Suzuki et al.

(10) Patent No.: US 10,368,935 B2
(45) Date of Patent: Aug. 6, 2019

(54) SURGICAL TREATMENT APPARATUS

(71) Applicant: OLYMPUS CORPORATION, Hachioji-shi, Tokyo (JP)

(72) Inventors: Tatsuya Suzuki, Hachioji (JP); Hideo Sanai, Hachioji (JP); Kenichi Kimura, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/495,306

(22) Filed: Apr. 24, 2017

(65) Prior Publication Data
US 2017/0224403 A1 Aug. 10, 2017

Related U.S. Application Data

(63) Continuation of application No. PCT/JP2015/074472, filed on Aug. 28, 2015.

(30) Foreign Application Priority Data

Oct. 28, 2014 (JP) .................. 2014-219630

(51) Int. Cl.
*A61B 18/04* (2006.01)
*A61B 18/00* (2006.01)
(Continued)

(52) U.S. Cl.
CPC ...... *A61B 18/04* (2013.01); *A61B 17/320068* (2013.01); *A61B 18/00* (2013.01);
(Continued)

(58) Field of Classification Search
CPC ........... A61B 2017/320069; A61B 2017/0046; A61B 2017/00106; A61B 2017/22011;
(Continued)

(56) References Cited

U.S. PATENT DOCUMENTS 5,391,144 A 2/1995 Sakurai et al.
5,712,543 A 1/1998 Sjostrom
(Continued)

FOREIGN PATENT DOCUMENTS

CN 103298419 A 9/2013
DE 197 00 270 A1 7/1998
(Continued)

OTHER PUBLICATIONS

Nov. 24, 2015 International Search Report issued in International Patent Application No. PCT/JP2015/074472.
(Continued)

*Primary Examiner* — Diane D Yabut
*Assistant Examiner* — Socrates L Boutsikaris
(74) *Attorney, Agent, or Firm* — Oliff PLC

(57) ABSTRACT

A surgical treatment apparatus includes a treatment portion unit; at least one operation portion provided in the treatment portion unit that is movable in response to an operation of an operator; a detection subject portion provided in the operation portion; a gripping portion that is detachable and attachable relative to the treatment portion unit; a non-contact type detection portion that is provided in the gripping portion separately from the operation portion and is capable of detecting an operation of the detection subject portion in accordance with the operation of the operation portion; an energy supply portion provided within the gripping portion, that supplies energy to the treatment portion; and a driving device connected to the gripping portion, that supplies energy to the energy supply portion in accordance with a detection result of the detection portion.

17 Claims, 18 Drawing Sheets

(51) Int. Cl.
*A61N 7/00* (2006.01)
*A61B 17/32* (2006.01)
*A61B 18/14* (2006.01)
*A61B 17/00* (2006.01)

(52) U.S. Cl.
CPC ............ *A61B 18/1402* (2013.01); *A61N 7/00* (2013.01); *A61B 2017/00876* (2013.01); *A61B 2018/00184* (2013.01); *A61B 2018/00928* (2013.01)

(58) Field of Classification Search
CPC ........ A61B 17/320068; A61B 17/2202; A61B 8/4477; A61B 2090/0804; A61B 2090/0805; A61B 2090/0806; A61B 2090/0813; A61B 2090/0814; A61M 2205/273
USPC .......................................................... 606/169
See application file for complete search history.

(56) References Cited

U.S. PATENT DOCUMENTS

| | | | |
|---|---|---|---|
| 2002/0183774 A1 | 12/2002 | Witt et al. | |
| 2003/0199794 A1* | 10/2003 | Sakurai | A61B 17/320068 601/2 |
| 2010/0298645 A1* | 11/2010 | Deutch | A61B 17/0218 600/201 |
| 2011/0288451 A1* | 11/2011 | Sanai | A61B 17/320092 601/2 |
| 2012/0110810 A1 | 5/2012 | Houser et al. | |
| 2012/0116388 A1* | 5/2012 | Houser | A61B 17/00234 606/41 |

FOREIGN PATENT DOCUMENTS

| | | |
|---|---|---|
| EP | 1 629 782 A1 | 3/2006 |
| JP | 2003-305050 A | 10/2003 |
| JP | 2009-189824 A | 8/2009 |
| JP | 4856290 B2 | 1/2012 |
| JP | 2014-513563 A | 6/2014 |

OTHER PUBLICATIONS

May 11, 2017 International Preliminary Report on Patentability received in International Application No. PCT/JP2015/074472.
May 15, 2018 Search Report issued in European Patent Application No. 15854938.6.
Jan. 3, 2019 Office Action issued in Chinese Patent Application No. 201580059293.3.

* cited by examiner

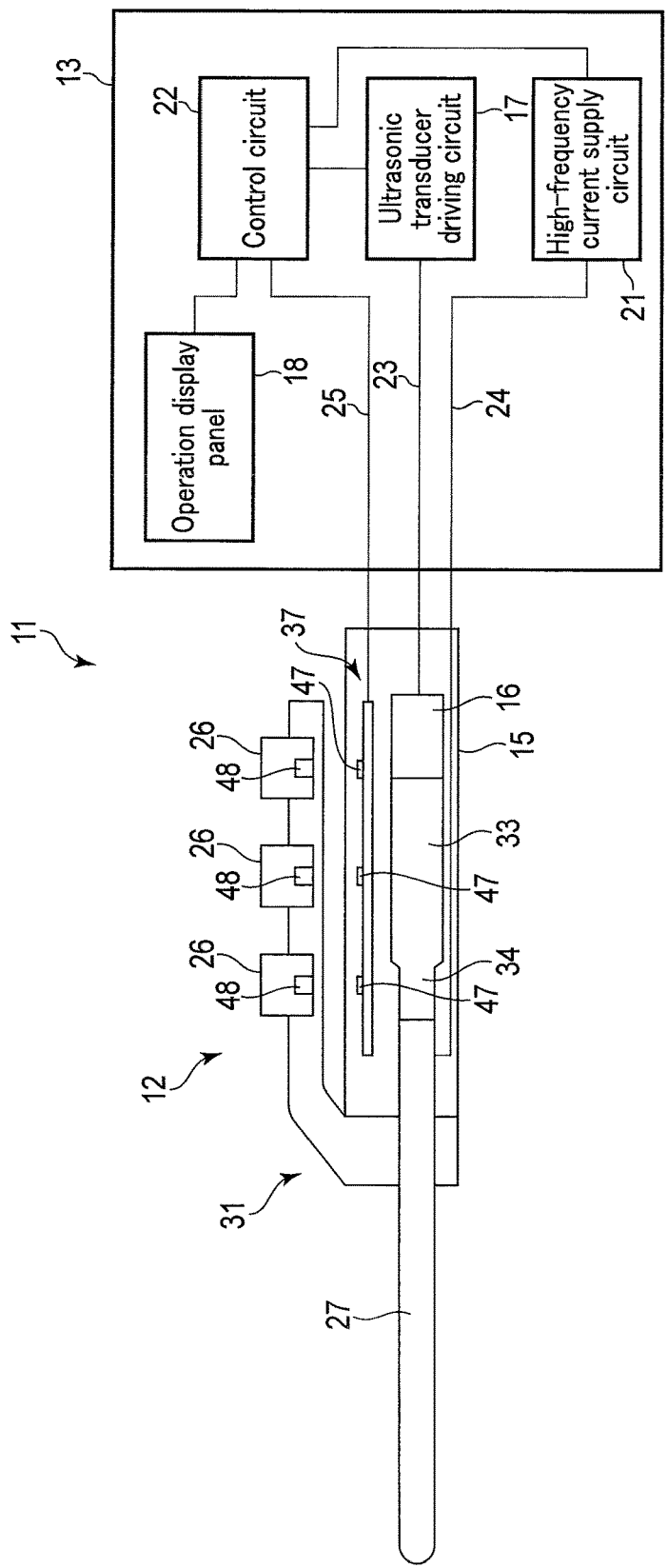
F I G. 2

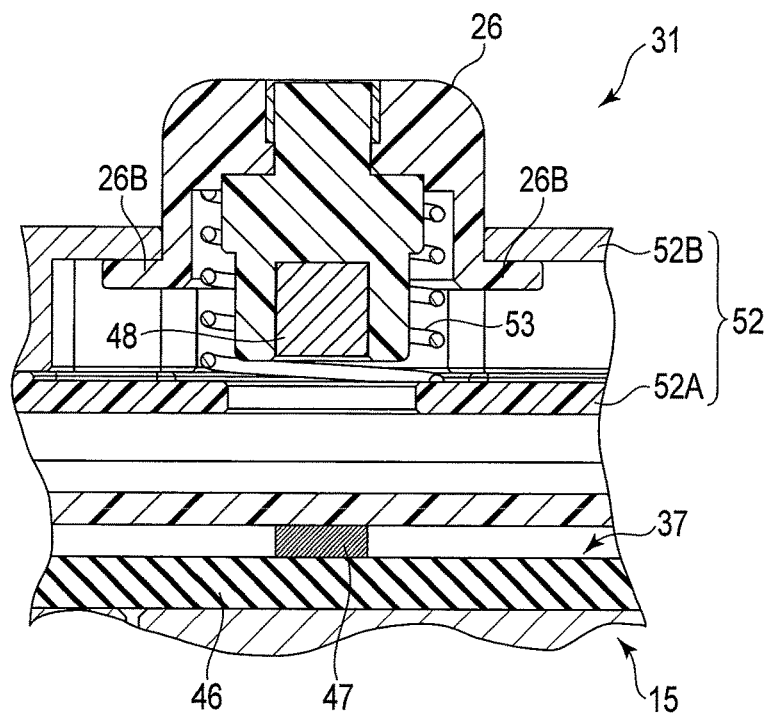
F I G. 7
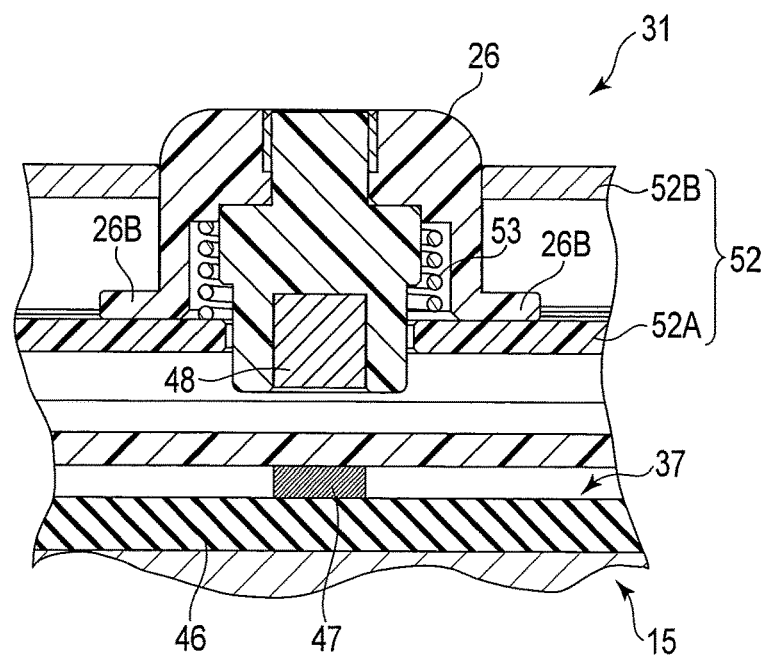
F I G. 8

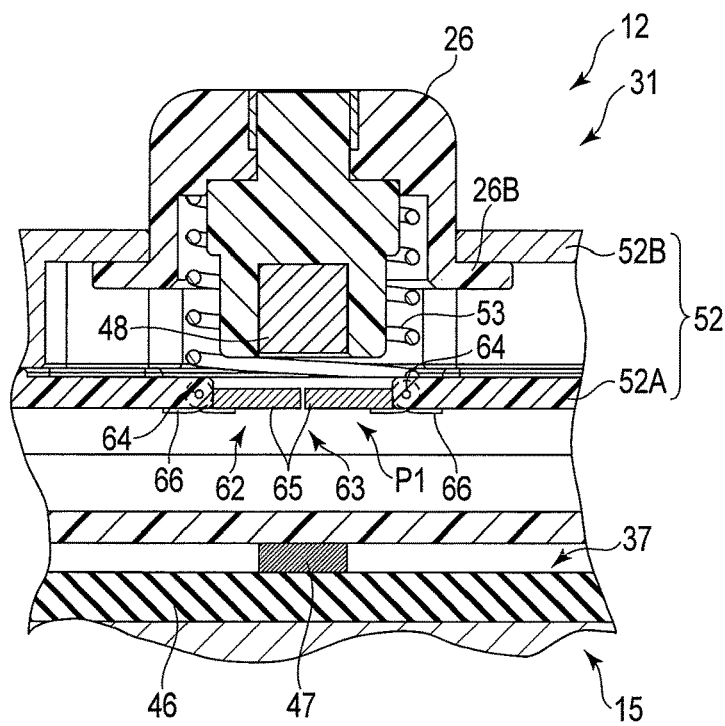
F I G. 15
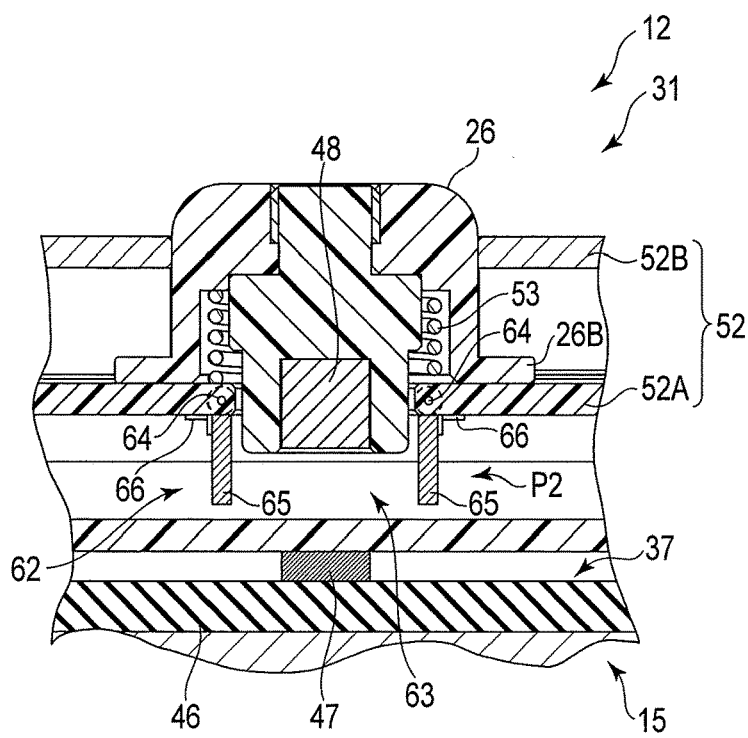
F I G. 16

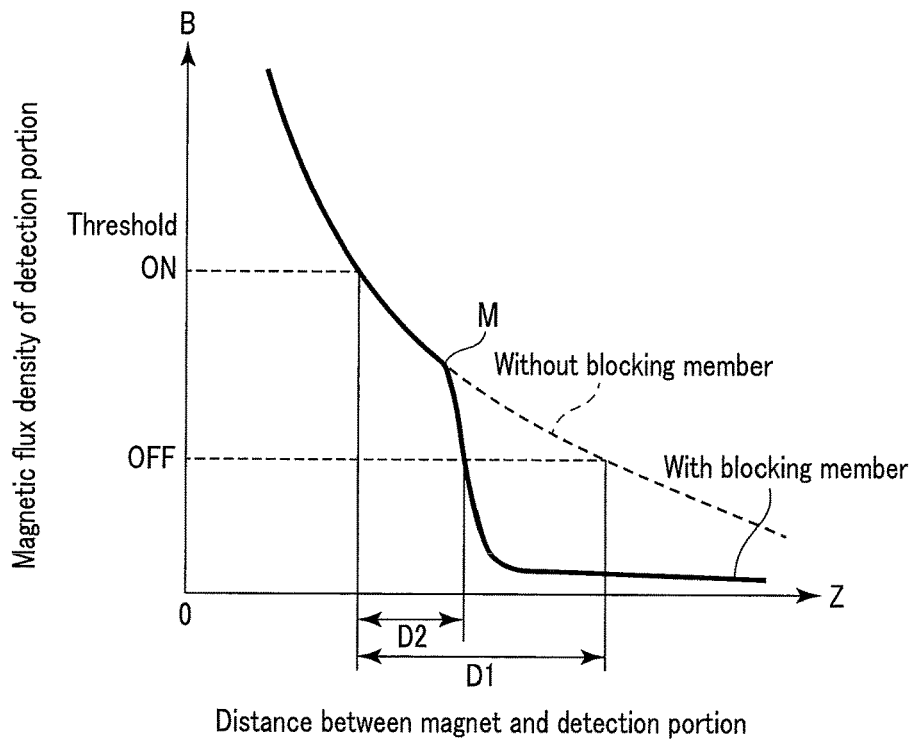
F I G. 17
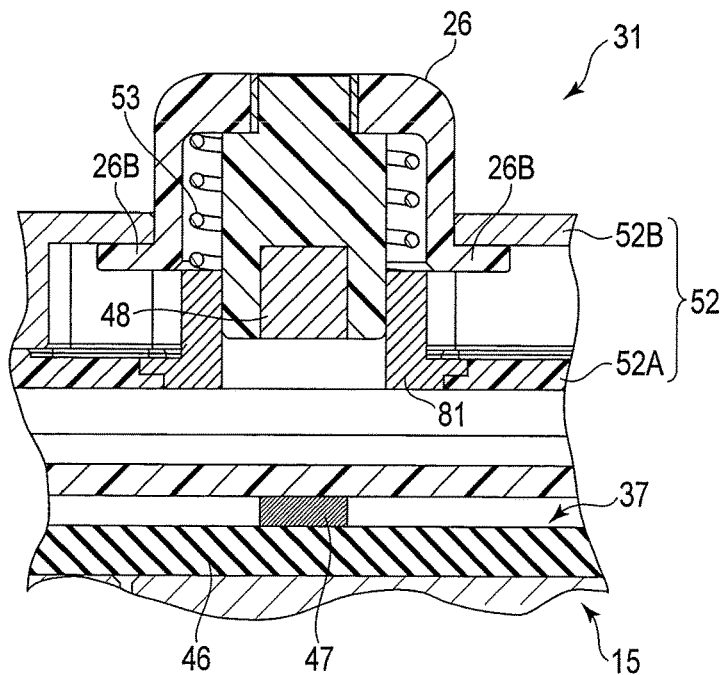
F I G. 18

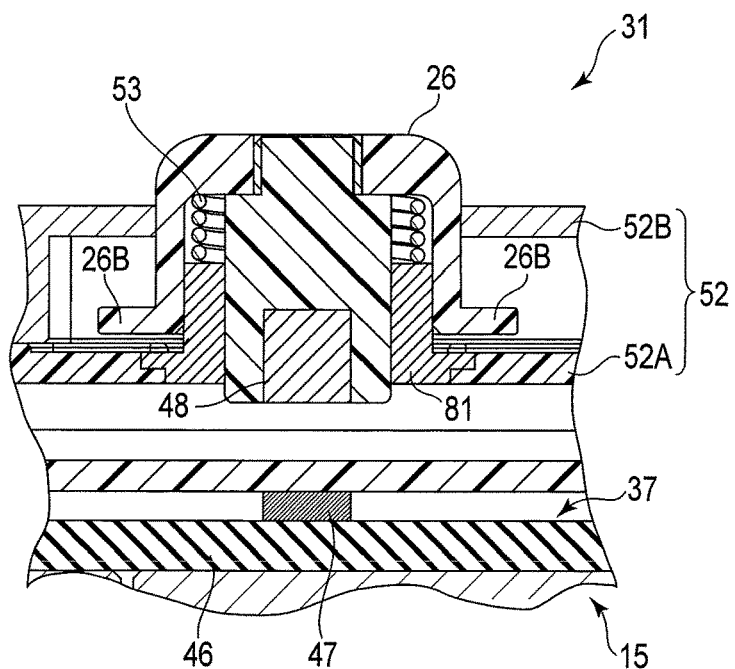
F I G. 19
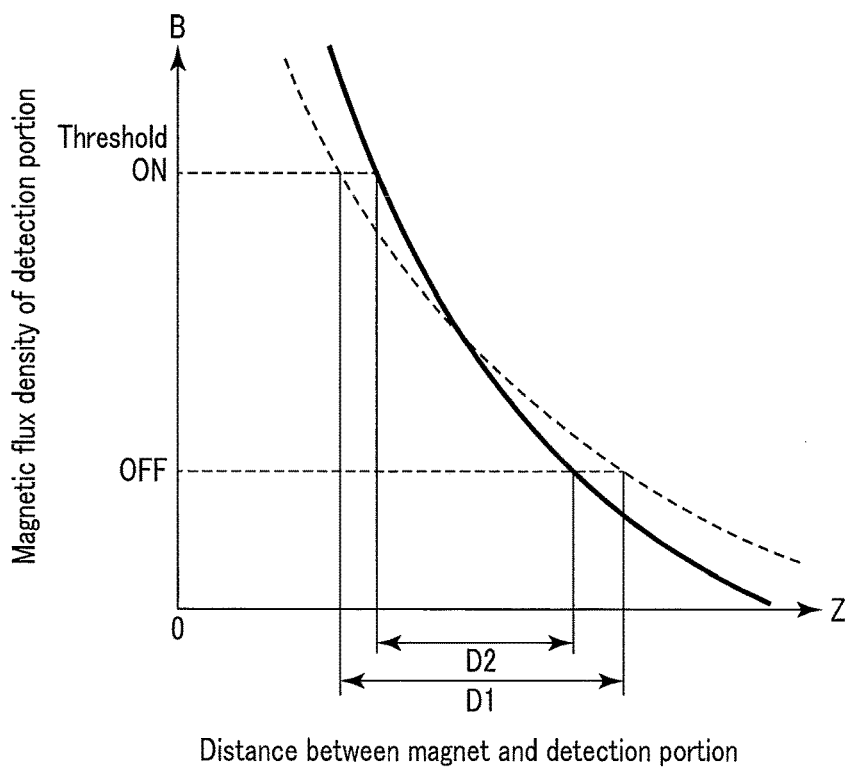
F I G. 20

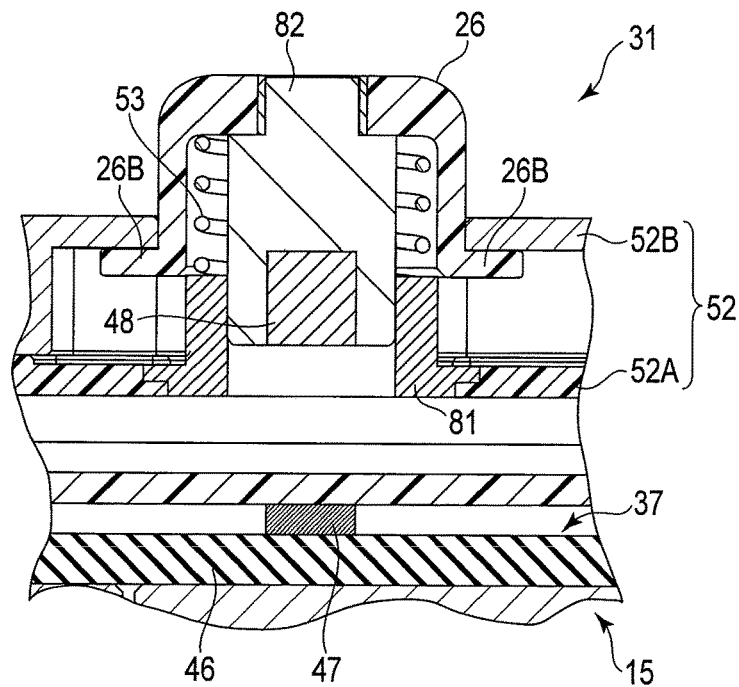
F I G. 21
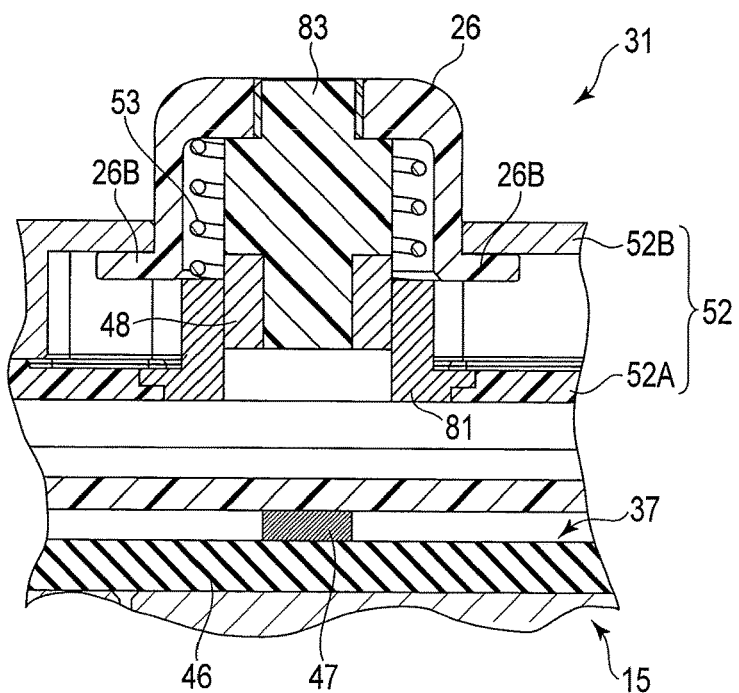
F I G. 22

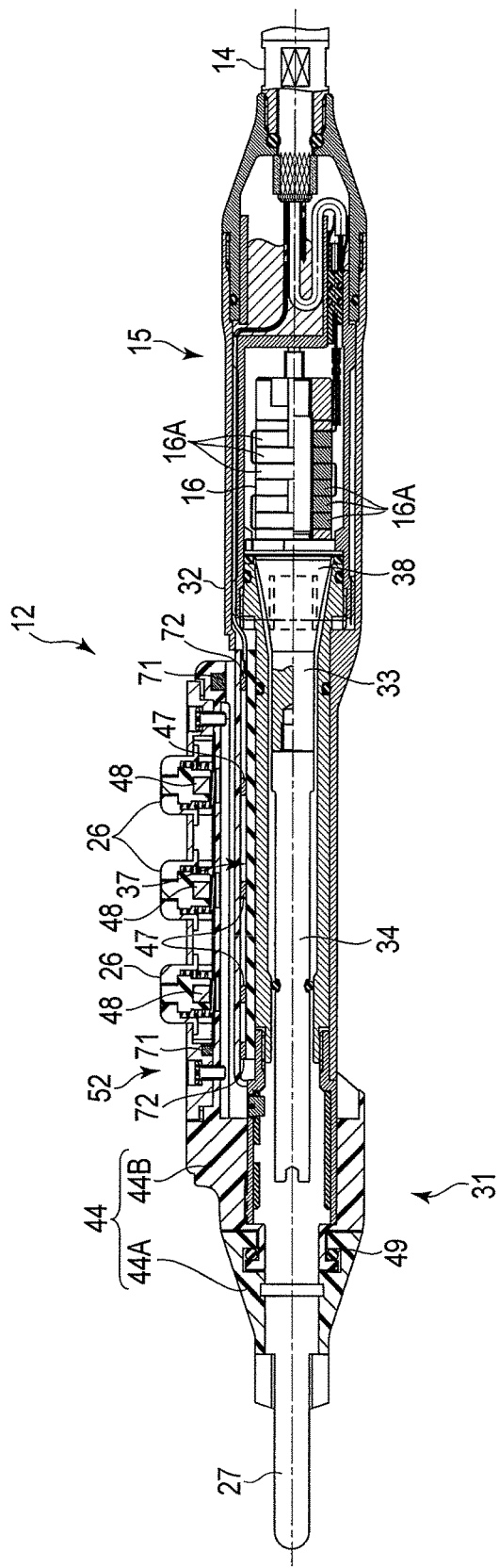
F I G. 23

SURGICAL TREATMENT APPARATUS

CROSS-REFERENCE TO RELATED APPLICATIONS

This application is a Continuation Application of PCT Application No. PCT/JP2015/074472, filed Aug. 28, 2015 and based upon and claiming the benefit of priority from prior Japanese Patent Application No. 2014-219630, filed Oct. 28, 2014, the entire contents of all of which are incorporated herein by reference.

BACKGROUND OF THE INVENTION

1. Field of the Invention

The present invention relates to a surgical treatment apparatus.

2. Description of the Related Art

U.S. Pat. No. 5,712,543 (Patent Literature 1) discloses a general surgical treatment apparatus. The surgical treatment apparatus uses the rotation power from the motor to perform treatment such as excision of a living tissue.

Such surgical treatment apparatuses include a main body which is repeatedly used after sterilization such as autoclaving, and the movable part that controls an output is covered by an elastic member such as a rubber.

BRIEF SUMMARY OF THE INVENTION

To achieve the aforementioned objective, a surgical treatment apparatus according to an aspect of the present invention includes a treatment portion unit having a treatment portion that performs treatment on a living tissue; at least one operation portion provided in the treatment portion unit that is movable in response to an operation of an operator; a detection subject portion provided in the operation portion; a gripping portion that is detachable and attachable relative to the treatment portion unit; a non-contact type detection portion that is provided in the gripping portion separately from the operation portion and is capable of detecting an operation of the detection subject portion in accordance with the operation of the operation portion; an energy supply portion provided within the gripping portion, that supplies energy to the treatment portion; and a driving device connected to the gripping portion, that supplies energy to the energy supply portion in accordance with a detection result of the detection portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram showing the connection relationship between a handpiece and a driving device of the surgical treatment apparatus shown in FIG. 1.

FIG. 7 is a cross-sectional view showing a push-button and a detection unit of the treatment portion unit shown in FIG. 6.

FIG. 8 is a cross-sectional view showing the push-button of the treatment portion unit shown in FIG. 7 when being pushed.

FIG. 15 is a cross-sectional view of a push-button and a blocking member of a surgical treatment apparatus according to the fifth embodiment.

FIG. 16 is a cross-sectional view showing a push-button shown in FIG. 15 when being pushed.

FIG. 17 is a graph showing the relationship between stroke distance D2 required for pushing the push-button of the surgical treatment apparatus according to the fifth embodiment and stroke distance D1 required for pushing the push-button when the blocking member is not provided.

FIG. 18 is a cross-sectional view of a push-button of a treatment portion unit, a detection unit and a ferromagnetic body of a surgical treatment apparatus according to the sixth embodiment.

FIG. 19 is a cross-sectional view showing a push-button shown in FIG. 18 when being pushed.

FIG. 20 is a graph showing the relationship between stroke distance D2 required for pushing the push-button of the surgical treatment apparatus according to the sixth embodiment and stroke distance D1 required for pushing the push-button when the ferromagnetic body is not provided.

FIG. 21 is a cross-sectional view of a push-button, a detection unit, and a ferromagnetic body of a treatment portion unit of a surgical treatment apparatus according to the first modification of the sixth embodiment.

FIG. 22 is a cross-sectional view of a push-button, a detection unit, and a ferromagnetic body of a treatment portion unit of a surgical treatment apparatus according to the second modification of the sixth embodiment.

FIG. 23 is a cross-sectional view of a handpiece of a surgical treatment apparatus according to the seventh embodiment, taken along a plane in a longitudinal axis.

DETAILED DESCRIPTION OF THE INVENTION

[First Embodiment]

The first embodiment of the present invention will be explained with reference to FIG. 1 to FIG. 10.

Figure 1:
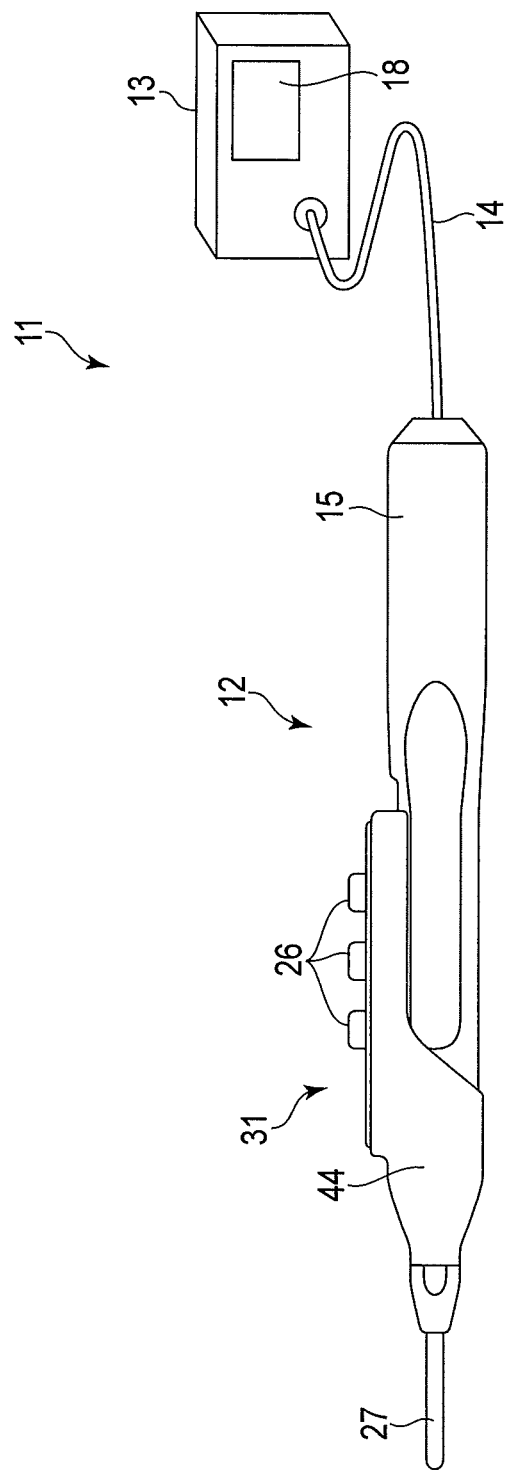
FIG. 1 is a schematic diagram showing the entire configuration of a surgical treatment apparatus according to the first embodiment.

As shown in FIG. 1, a surgical treatment apparatus 11 is provided with a handpiece 12, a driving device 13, and a cable 14 which connects the handpiece 12 and the driving device 13.

Figure 6:
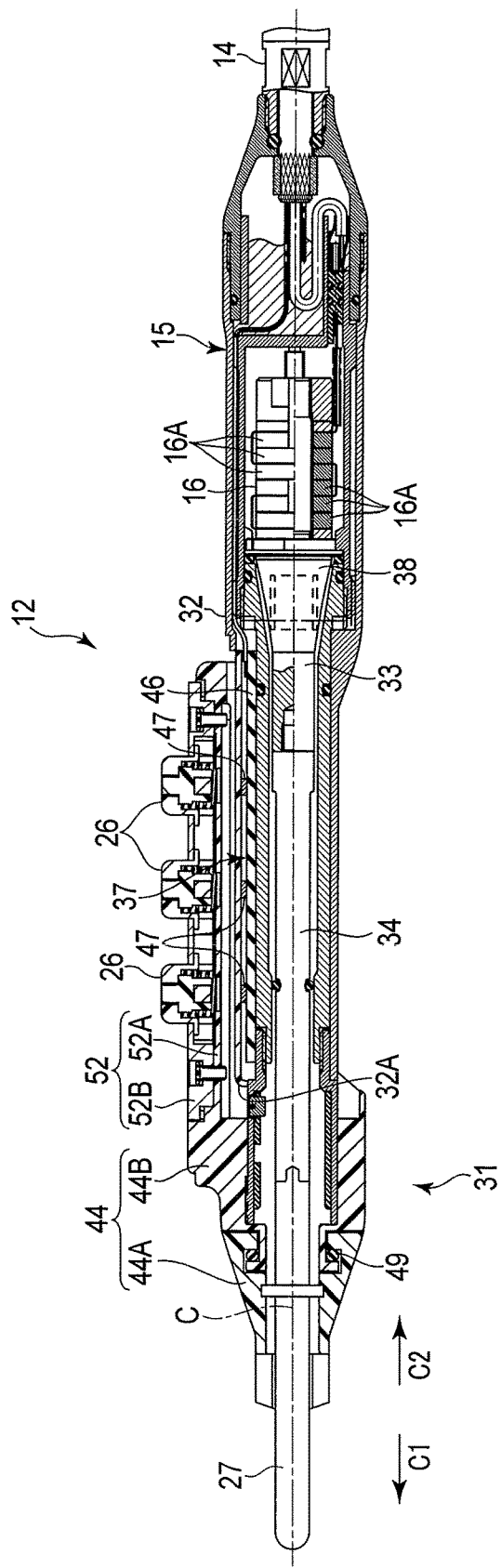
FIG. 6 is a cross-sectional view of the handpiece of the surgical treatment apparatus shown in FIG. 1, taken along a plane in a longitudinal axis.

As shown in FIGS. 2 and 6, the driving device 13 includes an ultrasonic transducer driving circuit 17 for driving a ultrasonic transducer 16 of a gripping portion 15, a high-frequency current supply circuit 21 for supplying a high-frequency current to a probe (treatment portion) 27 of the handpiece 12, an operation display panel 18 for setting or displaying an output level of an ultrasonic output or a high-frequency output corresponding to each push-button 26 of the handpiece 12, and a control circuit 22 connected thereto. The ultrasonic transducer driving circuit 17 is connected to a piezoelectric element 16A of the ultrasonic transducer 16 of a treatment portion unit 31 by two first leads 23 passing through the cable 14. The high-frequency current supply circuit 21 is connected to the probe 27 of the treatment portion unit 31 by a second lead 24 passing through the cable 14. The control circuit 22 is connected to a detection unit 37 of the treatment portion unit 31 by a plurality of third leads 25 passing through the cable 14.

The control circuit 22 is connected to the ultrasonic transducer driving circuit 17 and the high-frequency current supply circuit 21. If the push-button 26 is operated by a doctor, an electrical signal is transmitted to the control circuit 22, and the operation of the push-button 26 is detected. By this operation, the control circuit 22 controls the ultrasonic transducer driving circuit 17 to supply an ultrasonic generation current to the piezoelectric element 16A, or controls the high-frequency current supply circuit 21 to supply a high-frequency current to the probe 27. Accordingly, an ultrasonic vibration or a high-frequency current is transmitted to the probe 27. Otherwise, the control circuit 22 may simultaneously control both the ultrasonic transducer driving circuit 17 and the high-frequency current supply circuit 21 to simultaneously supply both an ultrasonic vibration and a high-frequency current to the probe 27.

The operation display panel 18 is a touch panel which is capable of various settings, for example, output level of ultrasonic output, output strength of high-frequency current, and functions of three push-buttons 26.

Figure 3:
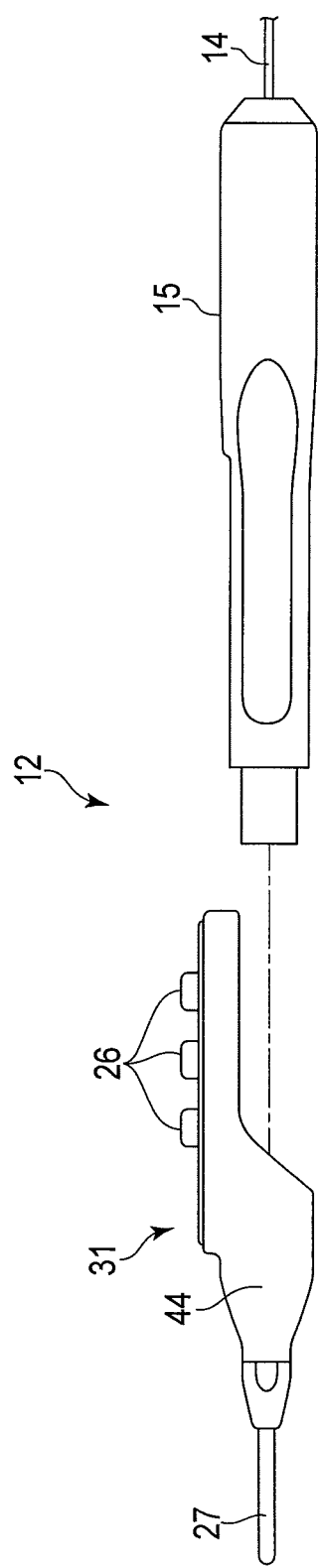
FIG. 3 is a schematic diagram showing the configuration where a treatment portion unit is attached to or detached from a gripping portion of the handpiece shown in FIG. 1.

As shown in FIGS. 1 to 3, the handpiece 12 is provided with the treatment portion unit 31 (disposable portion) including the probe 27 that applies treatment to a living tissue of a patient, and the gripping portion 15 (reusable portion) which is detachable relative to the treatment portion unit 31. The driving device 13 can generate energy to be transmitted to the treatment portion unit 31 along with the operation of the push-button 26 (operation portion).

Figure 4:
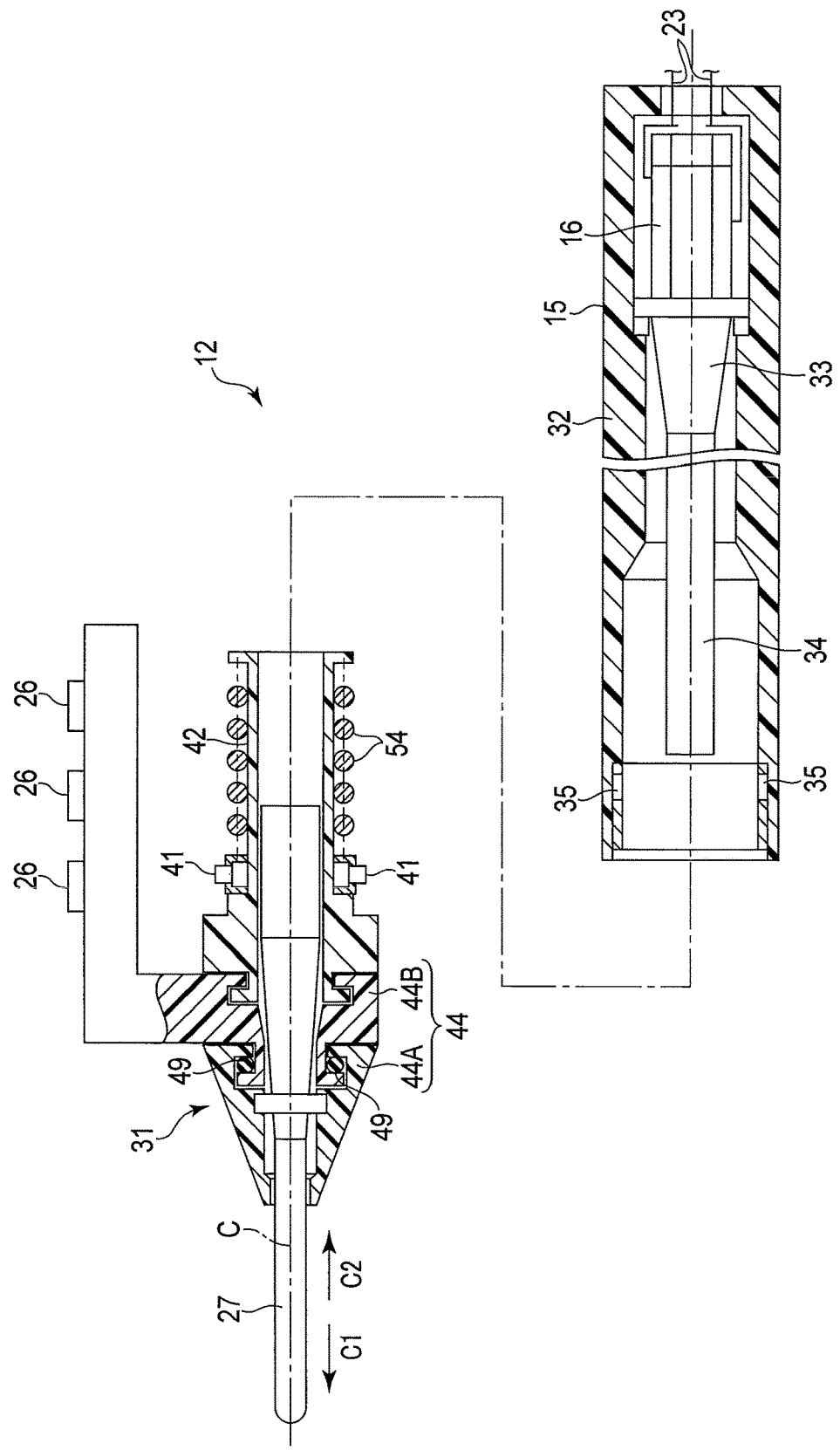
FIG. 4 is a cross-sectional view schematically showing the configuration where the treatment portion unit is attached to or detached from the gripping portion shown in FIG. 3.

As shown in FIGS. 4 and 6, the gripping portion 15 includes a housing 32 which has an essentially cylindrical shape and forms an outer shell, the ultrasonic transducer 16 housed in the housing 32, a horn member 33 connected to the ultrasonic transducer 16, a rod-shaped vibration transmitting member 34 extending from the horn member 33 and connected to the probe 27 of the treatment portion unit 31, a receiving portion 35 provided inside of the housing 32 to which a pin 41 at the treatment portion unit 31 side is hooked on, and a detection unit 37 capable of detecting an operation of the push-button 26 of the treatment portion unit 31. The gripping portion 15 is reusable after being cleaned and sterilized by autoclaving, etc. The vibration transmitting member 34 is formed of titanium, but may be formed of other metallic materials such as titanium alloy, duralumin, or stainless steel.

As shown in FIG. 6, the ultrasonic transducer 16 is a so-called bolt-clamped langevin transducer. The ultrasonic transducer 16 includes a plurality of ring-shaped piezoelectric elements 16A (six piezoelectric elements are adopted in this embodiment), and ultrasonic vibration can be generated from current provided from the ultrasonic transducer driving circuit 17 by the piezoelectric elements 16A. The ultrasonic transducer 16 is an example of an energy supply portion. The horn member 33 and the vibration transmitting member 34 are formed of a metallic material (for example, titanium). The horn member 33 may be formed of a metallic material other than titanium, such as titanium alloy, duralumin, or stainless steel. The horn member 33 is provided with a cross-sectional area variable portion 38 that has an essentially circular-cone shape, and the cross-sectional area of which reduces towards a distal end direction C1 of the probe 27. The ultrasonic vibration generated at the ultrasonic transducer 16 is transmitted to the horn member 33. The amplitude of the ultrasonic vibration is enlarged at the cross-sectional area variable portion 38.

Figure 5:
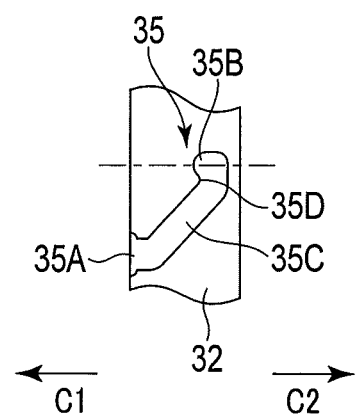
FIG. 5 is a schematic diagram showing a receiving portion provided in a housing of the gripping portion shown in FIG. 4.

As shown in FIG. 4, a pair of the receiving portions 35 are provided to respectively correspond to a pair of the pins 41 provided at the treatment portion unit 31 side and extending in the radial direction of the probe 27. As shown in FIG. 5, the receiving portion 35 is formed as a groove to which the pin 41 is hooked on. That is, the receiving portion 35 includes an introduction portion 35A to which the pin 41 is initially inserted, a holding portion 35B provided in the recess of the groove which forms the receiving portion 35, a guide portion 35C that connects the introduction portion 35A and the holding portion 35B, and a protruding portion 35D provided at a boundary between the holding portion 35B and the guide portion 35C.

When attaching the treatment portion unit 31 to the gripping portion 15, a cylindrical member 42 is inserted into the housing 32, and each pin 41 is inserted to the introduction portion 35A of the corresponding receiving portion 35, as shown in FIGS. 4 and 5. Then, the treatment portion unit 31 is rotated and pushed in relative to the gripping portion 15. If the pin 41 is inserted into the introduction portion 35A of the receiving portion 35, and the treatment portion unit 31 is rotated relative to the gripping portion 15, the pin 41 passes through the guide portion 35C to reach the holding portion 35B over the protruding portion 35D. In this case, the pin 41 slides in the direction of C2 relative to the probe 27, and compresses a spring member 54.

The urging force of the spring member 54 is applied to the probe 27 which is integrally formed with the cylindrical member 42 in the axial direction. By this process, the probe 27 is brought into contact with the vibration transmitting member 34 (the ultrasonic energy is transmitted to the probe 27 from the vibration transmitting member 34). Based on the above-explained detaching and attaching structure, when the treatment portion unit 31 is attached to the gripping portion 15, the treatment portion unit 31 can be positioned so that a detection subject portion 48 is placed within a range of being able to be detected by a detection portion 47.

On the other hand, in order to detach the treatment portion unit 31 from the gripping portion 15, the treatment portion unit 31 is rotated relative to the gripping portion 15 so that the pin 41 moves against the urging force of the spring member 54 and is removed from the holding portion 35B. By this process, the treatment portion unit 31 can be easily detached from the gripping portion 15.

As shown in FIGS. 2 and 6, the detection unit 37 includes a printed board 46 housed in a storage portion 32A of the housing 32, and a plurality of (three) detection portions 47 mounted on the printed board 46. The printed board 46 is formed as a hard plate. The detection portion 47 is a non-contact type sensor (magnetic sensor) provided separately from the push-button 26 at the treatment portion unit 31 side, and is capable of detecting an operation of the push-button 26 based on the position of the detection subject portion 48 (magnet) of the push-button 26. In the present embodiment, the detection portion 47 is formed of an integrated circuit in which a magnetic detection element, such as a Hall device, is mounted. If the strength of the magnetic field that the Hall device detects exceeds a predefined threshold, the integrated circuit outputs a predefined voltage corresponding to an energy supply start signal. If the strength of the magnetic field that the Hall device detects falls below the predefined threshold, the integrated circuit outputs a predefined voltage corresponding to an energy supply stop signal. The detection portion 47 is not limited to an integrated circuit in which a Hall device is mounted, but may be other non-contact type sensors such as a lead switch, an AMR sensor, etc.

As shown in FIGS. 4, 6, and 7, the treatment portion unit 31 includes the probe 27, a case 44 that covers the periphery of the probe 27, a button supporting portion 52, which has an essentially rectangular parallelepiped shape provided to protrude from an end portion of the case 44, a plurality of (for example, three) push-buttons 26 (operation portion), a plurality of spring members 53 that applies the reaction force to the push-buttons 26, the cylindrical member 42 integrally formed with the probe 27 and the case 44, and a spring member 54 formed of a compression spring.

As shown in FIG. 6, the probe 27 (treatment portion) is formed of a metallic material having biocompatibility (for example, titanium, titanium alloy, duralumin, stainless steel, etc.) as a rod-like shape. In the present embodiment, it is assumed that one of the directions in a longitudinal axis C of the probe 27 is a distal end direction C1, and the other direction that is opposite to the distal end direction C1 is a proximal end direction C2. The proximal end of the probe 27 abuts on and is joined to the distal end of the vibration transmitting member 34. The probe 27 receives ultrasonic vibration transmitted from the ultrasonic transducer 16, and a high-frequency current supplied from the high-frequency current supply circuit 21 through the second lead 24. Accordingly, the probe 27 is capable not only of applying an ultrasonic vibration to a living tissue, but also of functioning as a first electrode of a unipolar electrocautery. The surgical treatment apparatus 11 further includes a return electrode plate that is placed outside the body of a patient, and functions as a second electrode of the unipolar electrocautery.

The case 44 is formed, for example, of a synthetic resin material. The case 44 includes a first part 44A, a second part 44B, and a plurality of balls 49 each provided at a connected portion of the first part 44A and the second part 44B. The first part 44A is integrally fixed to the probe 27. The first part 44A and the probe 27 can be rotated around the central axis C relative to the second part 44B. The first part 44A functions as a sheath that covers part of the outer peripheral of the probe 27.

As shown in FIGS. 6 and 7, the button supporting portion 52 is integrally formed with the second part 44B. The button supporting portion 52 has a base portion 52A integrally formed with the case 44, and a cover 52B that is put on the base portion 52A. The three push-buttons 26 and the three spring members 53 are sandwiched and held between the base portion 52A and the cover 52B. The base portion 52A and the cover 52B are fixed by a screw. The spring member 53 is formed of a coil spring, but not limited thereto. The spring member 53 may be formed of a disc spring, a metal dome, a rubber dome, etc.

The plurality of balls 49 are provided at appropriate intervals around the central axis C, in order to reduce friction between the first part 44A and the second part 44B. It is possible to provide a bearing such as a thrust ball bearing which permits rotation or turning around the central axis C2, between the first part 44A and the second part 44B, instead of the balls 49. In addition, instead of the balls 49 or the thrust ball bearing, a lubricating sheet material or an oilless bush, for example, may be disposed between the first part 44A and the second part 44B.

The push-button 26 has an edge portion 26B that prevents the push-button 26 from being dropped from the cover 52B (see FIG. 7). The push-button 26 includes the detection subject portion 48 at the bottom part, which is detected by the detection unit 37 at the gripping portion 15 side. The detection subject portion 48 is formed, for example, of a magnet. The magnet used for the detection subject portion 48 is, for example, a neodymium magnet. The magnet used for the detection subject portion 48 is not limited to the neodymium magnet, but may be other types of magnets such as a samarium-cobalt magnet, a ferrite magnet, an alnico magnet, etc. The push-button 26 is an example of the operation portion.

In the present embodiment, the push-button 26 arranged closest to the distal end direction C1 is assigned to a cutting mode by a high-frequency current, for example. The push-button 26 arranged in the middle is assigned to a first coagulation mode by two types of energy such as a high-frequency current and ultrasonic vibration, for example. The push-button 26 arranged closest to the proximal end direction C2 is assigned to a second coagulation mode by a high-frequency current, for example. The aforementioned function of each push-button 26 is merely an example. The function assigned to each push-button 26 may be appropriately set or changed by using the operation display panel 18 of the driving device 13. The spring member 53 outwardly urges the push-button 26.

Next, the procedure when the push-button 26 of the present embodiment is operated will be described with reference to FIGS. 7 and 8. When a doctor pushes a push-button 26, the detection portion 47 of the detection unit 37 detects that the magnetic field is intensified, and sends an ON signal to the control circuit 22 of the driving device 13. The control circuit 22 performs the processing corresponding to the ON signal (transmitting a signal to the high-frequency current supply circuit 21, and supplying a high-frequency current corresponding to an incision mode from the high-frequency current supply circuit 21).

On the other hand, when a doctor removes his finger from the push-button 26, the detection portion 47 of the detection unit 37 detects that the magnetic field is weakened, and sends an OFF signal to the control circuit 22 of the driving device 13. The control circuit 22 performs the processing corresponding to the OFF signal (stopping supply of a high-frequency current, etc.).

The procedure in which the magnet that is the detection subject portion 48 is thermally demagnetized when a user performs sterilization on the treatment portion unit 31, will be explained with reference to FIG. 9. The treatment portion unit 31 of the present embodiment is a disposal part that is assumed to be used only once, and is devised to prevent the unit from being erroneously reused.

Generally, if thermal energy is applied to a magnet, magnetic particles (magnetic moments) forming the magnet vibrate, and the directions of fine magnets become uneven. In addition, if a magnet is heated to a temperature, called the Curie temperature, the directions of magnetic particles become completely random, and the magnetic force is completely removed even if the magnet is returned to room temperature afterward. The phenomena in which the magnetic force of a magnet is removed due to a high temperature is called thermal demagnetization.

Figure 9:
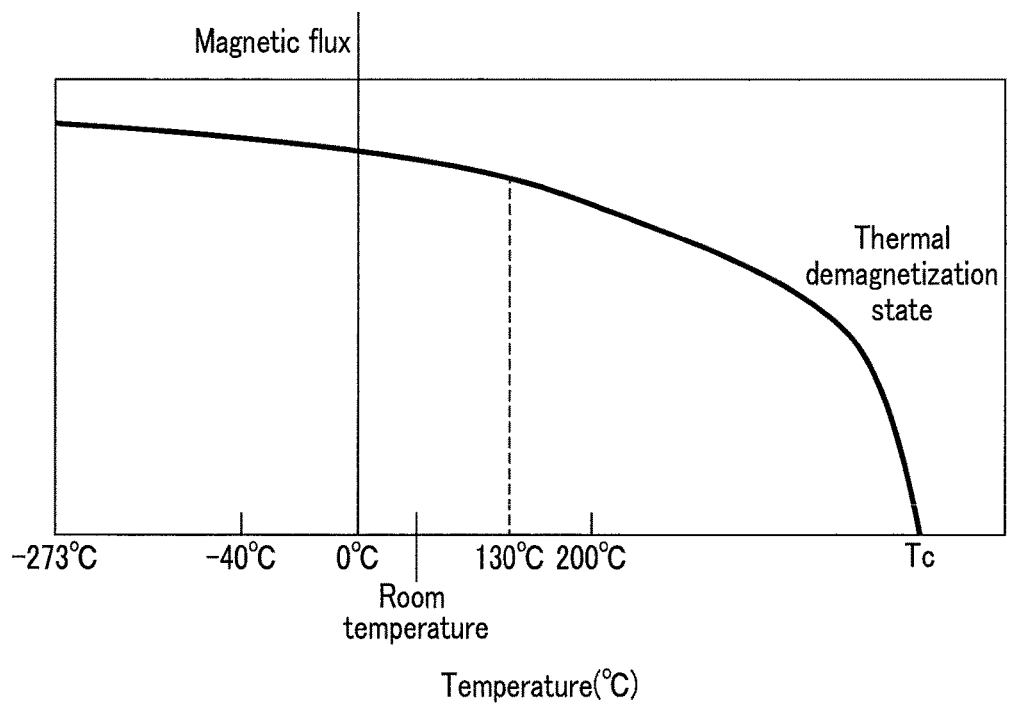
FIG. 9 is a graph showing thermal demagnetization of a detection subject portion (magnet) of the push-button shown in FIG. 7.
Figure 10:
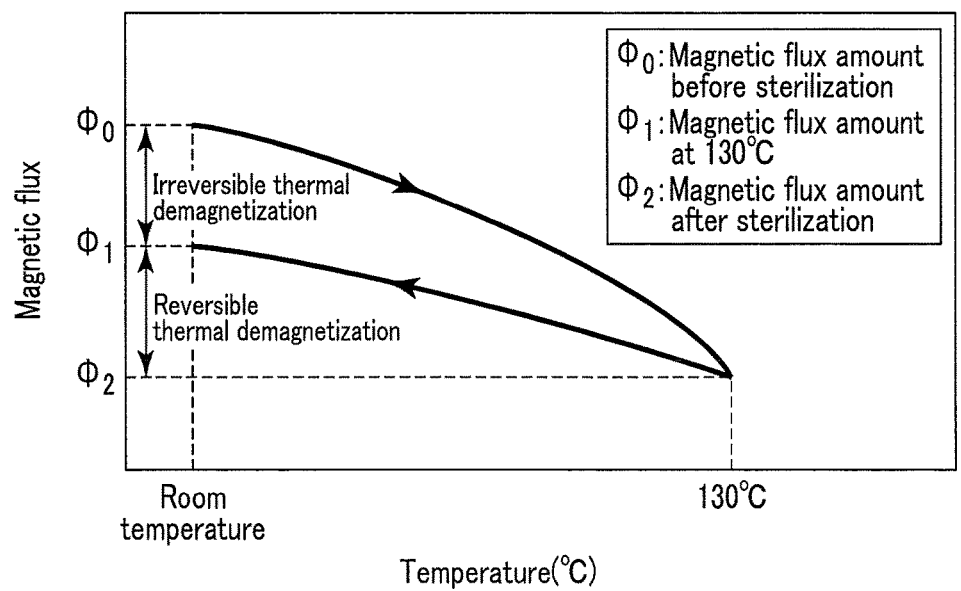
FIG. 10 is a graph schematically showing that part of the magnetic force of the detection subject portion (magnet) of the push-button shown in FIG. 7 is removed by thermal demagnetization.

In the surgical treatment apparatus 11 of the present embodiment, if a user performs a sterilization process such as autoclaving (approximately at 130° C.) relative to the treatment portion unit 31, part of the magnetic force of the magnet that is the detection subject portion 48 is irreversibly removed by thermal demagnetization, as shown in FIGS. 9 and 10. Specifically, the magnetic force of the magnet of the detection subject portion 48 falls below a threshold of a magnetic flux density based on which the detection portion 47 detects the push-button 26 being pushed. By this process, even if the treatment portion unit 31 subjected to autoclaving or the like is attached to the gripping portion 15, and the doctor operates the push-button 26, the operation of the push-button 26 is not detected by the detection unit 37. Accordingly, the treatment portion unit 31 is prevented from being reused.

According to the present embodiment, the handpiece 12 is provided with the treatment portion unit 31, the operation portion that is provided in the treatment portion unit 31, the gripping portion 15 that is detachable and attachable relative to the treatment portion unit 31 and supplies energy to the treatment portion unit 31 in accordance with the operation of the operation portion, and the non-contact type detection portion 47 that is provided in the gripping portion 15 separately from the operation portion and is capable of detecting the operation of the operation portion.

With the above configuration, the operation portion and the detection portion 47 are isolated, and the detection portion 47 is a non-contact type. Accordingly, there is no need to open or close a circuit by mechanically varying part of a switch structure as needed for a mechanical switch such as a tactile switch, and the switching is realized only by the movement of the detection subject portion 48. Thus, the required force (operation force) for operating the operation portion can be reduced. In addition, since a movable portion (operation portion) is provided in the treatment portion unit 31 side which is disposable, there is no need to interpose a sealing member in the operation portion to have resistance against cleaning, disinfecting, and sterilizing processes.

Thus, the operation force of the operation portion can also be reduced in this point. Furthermore, since the treatment portion unit is disposable, consistently stable operation force can be realized. In addition, because a switch board or an electrical contact for a switch is not provided on the treatment portion unit 31 side, the treatment portion unit 31 can be downsized. Accordingly, the cost of the disposable treatment portion unit 31 can be reduced, and the cost for a surgical operation can be reduced. On the other hand, since a movable portion is not provided in the gripping portion 15, the cleaning and sterilizing process of the reusable gripping portion 15 can be efficiently performed.

The operation portion includes the detection subject portion 48 which is detected by the detection portion 47. The detection subject portion 48 cannot be detected by the detection portion 47 if the treatment portion unit 31 is subjected to the sterilization process. In the general surgical treatment apparatus, the treatment portion that is brought into contact with a living tissue of a patient is assumed to be disposed since it is difficult to clean all of the large amount of tissue fragments attached during the operation of the treatment portion, and it is difficult to realize excellent performance with a reusable structure. According to the aforementioned configuration, if the treatment portion unit 31 subjected to sterilization is to be reused, the detection subject portion 48 cannot be detected by the detection portion 47, thereby preventing the treatment portion unit 31 from being reused.

According to the present embodiment, the detection subject portion 48 is a magnet, and the detection portion is a magnetic detection element. With this configuration, the detection subject portion 48 becoming undetectable due to sterilization can be easily realized.

[Second Embodiment]

Figure 11:
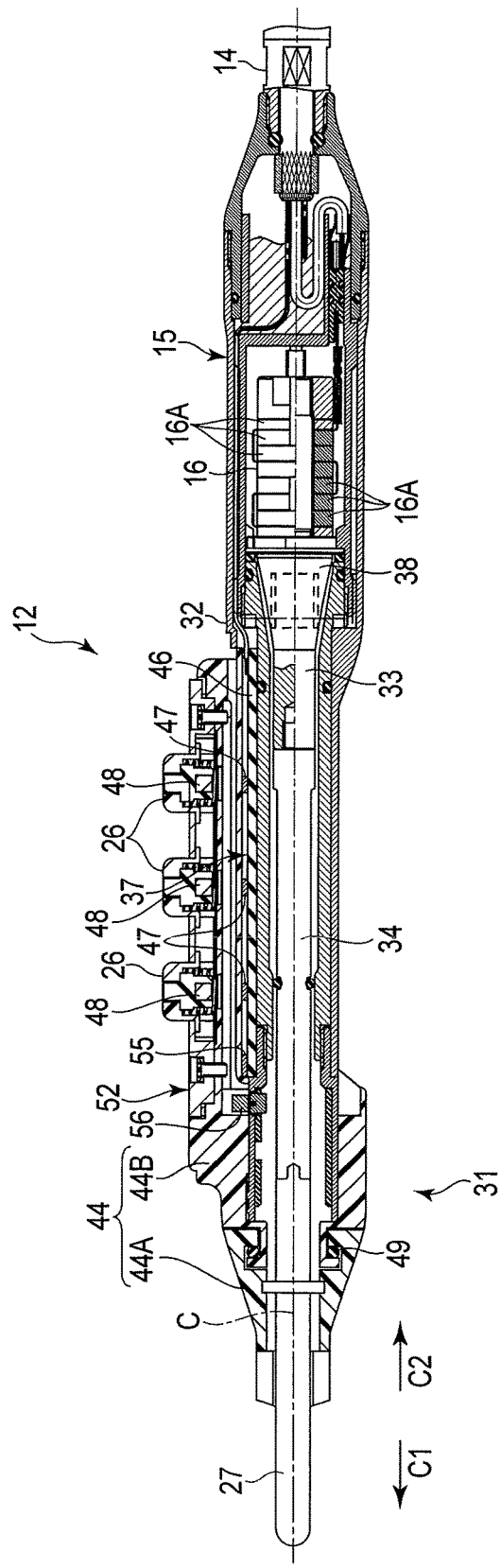
FIG. 11 is a cross-sectional view of a handpiece of a surgical treatment apparatus according to the second embodiment, taken along a plane in a longitudinal axis.

A surgical treatment apparatus according to the second embodiment will be described with reference to FIG. 11. A surgical treatment apparatus 11 of the second embodiment is different from the surgical treatment apparatus 11 of the first embodiment only in that a second detection element 55 which is an attachment detection portion is provided in a gripping portion 15. Accordingly, mainly those portions different from the first embodiment will be explained, and portions the same as the first embodiment will not be explained or shown in the drawings.

A detection unit 37 includes a printed board 46 housed in a storage portion 32A of a housing 32, and a detection portion 47 and a second detection element 55 mounted on the printed board 46. The detection portion 47 has the same configuration as that of the first embodiment.

The second detection element 55 is a non-contact type sensor (magnetic sensor), and is capable of detecting a position of the second detection subject portion 56 (magnet) at the treatment portion unit 31 side. The second detection element 55 is provided at the outermost position of the probe 27 in the distal end direction C1 on the printed board 46. The second detection element 55 is an example of an attachment detection portion that is capable of detecting that the treatment portion unit 31 is attached to the gripping portion 15. In the present embodiment, the second detection element 55 is formed of a Hall device, for example. The second detection element 55 is not limited to a Hall device, but may be other non-contact type sensors such as a lead switch and an AMR sensor, etc.

The second detection subject portion 56 is provided in a case 44 of the treatment portion unit 31. The second detection subject portion 56 is mounted into a recess provided on an inner peripheral surface of the cylindrical case 44. The second detection subject portion 56 is formed, for example, of a magnet. The magnet used for the second detection subject portion 56 is, for example, a neodymium magnet. The magnet used for the second detection subject portion 56 is not limited to the neodymium magnet, but may be other types of magnets such as a samarium-cobalt magnet, a ferrite magnet, an alnico magnet, etc.

If the treatment portion unit 31 is correctly attached to the gripping portion 15, the second detection subject portion 56 of the treatment portion unit 31 is positioned close to the second detection element 55 of the gripping portion 15. By this positioning, the second detection element 55 detects that the magnetic field is intensified, and sends an attachment detection signal to a control circuit 22 of a driving device 13. The driving device 13 that has received the attachment detection signal can sense that the treatment portion unit 31 is correctly attached to the gripping portion 15.

On the other hand, if the treatment portion unit 31 is detached from the gripping portion 15, the second detection subject portion 56 of the treatment portion unit 31 is taken away from the second detection element 55 of the gripping portion 15. By this process, the second detection element 55 detects that the magnetic field is weakened, and sends an attachment cancellation signal to the control circuit 22 of the driving device 13. The driving device 13 that has received the attachment cancellation signal can sense that the treatment portion unit 31 is detached from the gripping portion 15.

According to the present embodiment, the surgical treatment apparatus 11 includes the attachment detection portion provided in the gripping portion 15; the attachment detection portion being capable of detecting that the treatment portion unit 31 is attached to the gripping portion 15.

With this configuration, the operation of the operation portion is enabled only when the treatment portion unit 31 is correctly attached to the gripping portion 15. Accordingly, a situation in which energy is supplied to the treatment portion unit 31 in the state where the treatment portion unit 31 is attached to the gripping portion 15 at an incorrect angle (i.e., mounting failure state) can be prevented from occurring.

[Third Embodiment]

Figure 12:
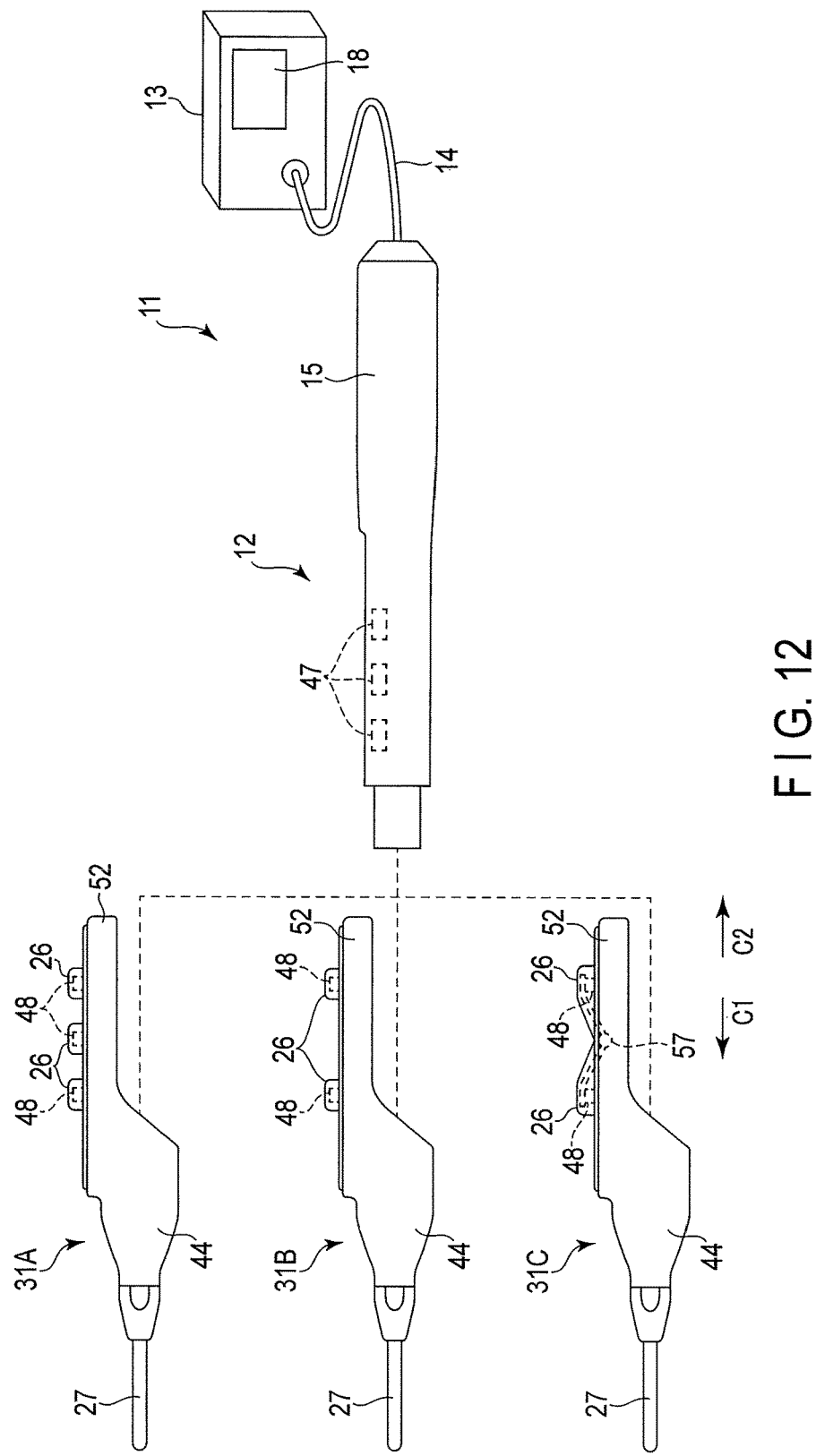
FIG. 12 is a schematic diagram showing the entire configuration of a surgical treatment apparatus according to the third embodiment.

A surgical treatment apparatus according to the third embodiment will be described with reference to FIG. 12. A surgical treatment apparatus 11 of the third embodiment is only different from the surgical treatment apparatus 11 of the first embodiment in that one of a treatment portion unit 31A and second treatment portion units 31B and 31C is provided in a gripping portion 15. Accordingly, mainly those portions different from the first embodiment will be explained, and portions that are the same as the first embodiment will not be explained or shown in the drawings.

In the present embodiment, one of the treatment portion unit 31A and second treatment portion units 31B and 31C can be selected and mounted on the gripping portion 15. In the present embodiment, the configuration of the treatment portion unit 31A is the same as the treatment portion unit 31 of the first embodiment.

Each of the second treatment portion units 31B and 31C are different from the treatment portion unit 31A in the shape of a button supporting portion 52, the number, shape, and arrangement of push-buttons 26 provided in the button supporting portion 52, but are the same as the treatment portion unit 31A in the other portions. That is, the treatment portion unit 31A includes two push-buttons 26 (second operation portions), and a button supporting portion 52, which is an essentially rectangular parallelepiped shape configured to support the two push-buttons 26. The shape of each push-button 26 is the same as that of the first embodiment. However, the function assigned to each push-button 26 is different from that in the first embodiment.

In the second treatment portion unit 31B, the push-button 26 arranged closest to the distal end direction C1 is, for example, assigned to a cutting mode by a high-frequency current. The push-button 26 arranged closest to the proximal end direction C2 is, for example, assigned to a coagulation mode by a high-frequency current. That is, the treatment portion unit 31B reduces the number of push-buttons 26 to simplify the function and the shape.

The second treatment portion unit 31C includes two rocker switches 26, a button supporting portion 52, which is an essentially rectangular parallelepiped shape configured to support the two rocker switches 26, and a supporting member 57, which is formed as a seesaw-like form, attached rotatably to the button supporting portion 52.

The supporting member 57 is arranged to span across both of the two rocker switches 26. The supporting member 57 is attached rotatably to the button supporting portion 52 by a fulcrum portion. By means of the supporting member 57, an erroneous operation where both two rocker switches 26 are pushed at the same time can be prevented.

In the second treatment portion unit 31C, the push-button 26 arranged closest to the distal end direction C1 is, for example, assigned to a cutting mode by a high-frequency current. The push-button 26 arranged closest to the proximal end direction C2 is, for example, assigned to a coagulation mode by a high-frequency current.

As stated above, the treatment portion unit 31A, and the second treatment portion units 31B and 31C are different in the number, shape, and arrangement of the operation portions. The aforementioned function assigned to each operation portion 26 of the treatment portion unit 31A, and the second treatment portion units 31B and 31C, is an example. The function assigned to each operation portion 26 of the treatment portion unit 31A, and the second treatment portion units 31B and 31C, may be appropriately set or changed by using the operation display panel 18 of the driving device 13. In addition, the shape of the probe (treatment portion) of the treatment portion unit 31A is the same as the shape of the probe 27 (second treatment portion) of the second treatment portion units 31B and 31C. The treatment portion unit 31A, and the second treatment portion units 31B and 31C may be mutually different in the probe shape (for example, knife-shape, hook-shape, spatula-shape, etc.), and in the probe length.

According to the third embodiment, a plurality of second treatment portion units, one of which can be selectively detached and attached relative to the gripping portion, are provided instead of the treatment portion unit. The second treatment portion units are different in the number, shape, and arrangement of the operation portions, and/or are different in the length and shape of the probe. With this configuration, a treatment portion unit can be selected and attached to the gripping portion 15 among the various kinds of treatment portion units: the treatment portion unit 31A; and the second treatment portion units 31B and 31C, depending on the use or user's preference. Thus, the surgical treatment apparatus 11 can be used for various surgical operations, and convenience for the doctor can be remarkably improved.

[Fourth Embodiment]

Figure 13:
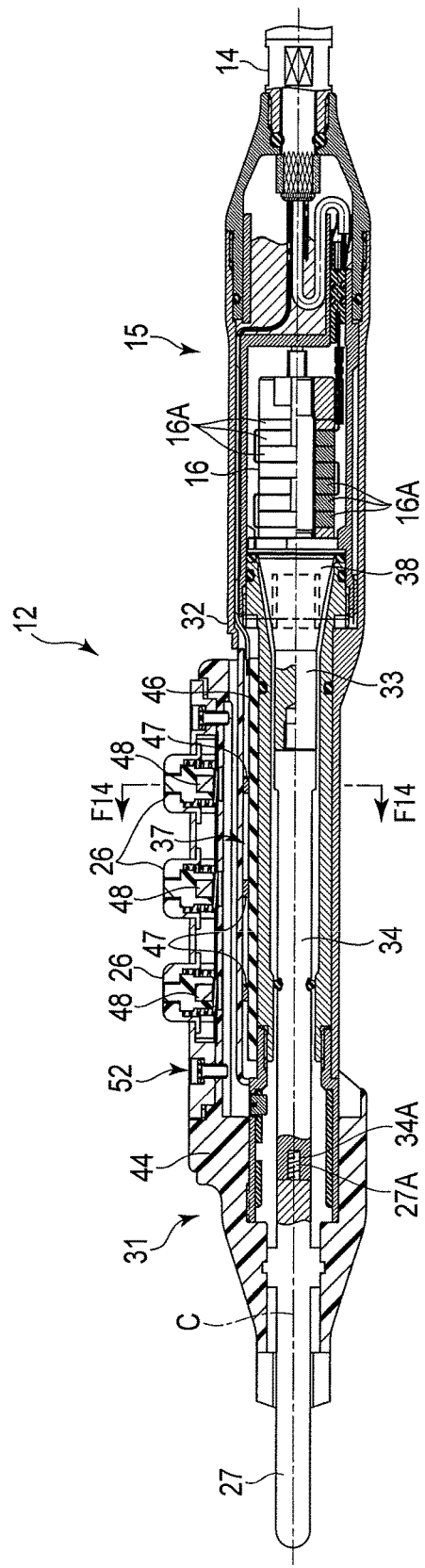
FIG. 13 is a cross-sectional view of a handpiece of a surgical treatment apparatus according to the fourth embodiment, taken along a plane in a longitudinal axis.

A surgical treatment apparatus according to the fourth embodiment will be described with reference to FIGS. 13 and 14. A surgical treatment apparatus 11 of the fourth embodiment is different from the surgical treatment apparatus 11 of the first embodiment only in that a treatment portion unit 31 is fixed to a gripping portion 15 by means of a screw. Accordingly, mainly those portions different from the first embodiment will be explained, and portions the same as the first embodiment will not be explained or shown in the drawings.

The gripping portion 15 includes a housing 32 which has an essentially cylindrical shape and forms an outer shell, an ultrasonic transducer 16 housed in the housing 32, a horn member 33 connected to the ultrasonic transducer 16, a rod-shaped vibration transmitting member 34 extending from the horn member 33 and connected to a probe 27 of the treatment portion unit 31, and a detection unit 37 capable of detecting an operation of a push-button 26 of the treatment portion unit 31 on the entire perimeter of the gripping portion 15 around the longitudinal axis.

The vibration transmitting member 34 is provided at the end with an internal thread portion 34A to which an external thread portion 27A at the probe 27 side is to be fixed. The vibration transmitting member 34 is formed of a metallic material (for example, titanium). The vibration transmitting member 34 may be formed of a metallic material other than titanium, such as a titanium alloy, duralumin, or stainless steel.

In the present embodiment, a printed board 46 of the detection unit 37 is formed of a flexible printed wiring board which has flexibility, which is different from the first embodiment. A plurality of detection portions 47 are mounted on the printed board 46 of the detection unit 37. The detection portion 47 includes an element which is a non-contact type sensor (magnetic sensor), and is capable of detecting a position of a detection subject portion 48 (magnet) at the treatment portion unit 31 side. In the present embodiment, the detection portion 47 is formed of a Hall device, for example. The detection portion 47 is not limited to a Hall device, but may be another non-contact type sensor such as a lead switch and an AMR sensor, etc.

Figure 14:
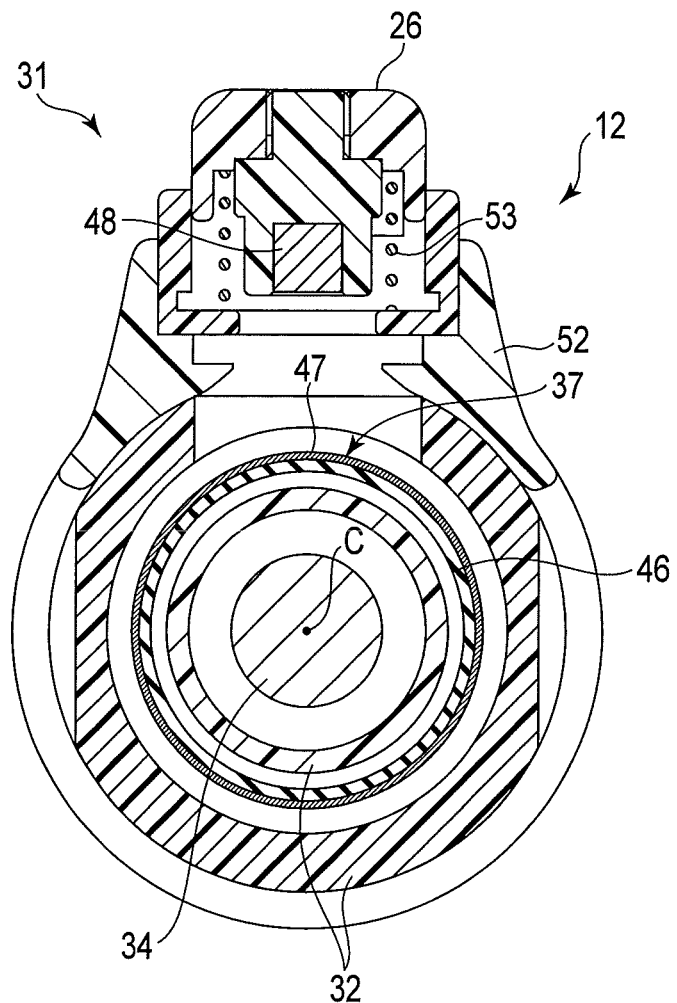
FIG. 14 is a cross-sectional view taken along line F14-F14 in FIG. 13.

In the present embodiment, the detection portions 47 are arranged at the same position in the longitudinal direction (central axis C direction) of the probe 27, i.e., on a single circumference whose center is on a central axis C of the vibration transmitting member 34 (probe 27, gripping portion 15), as shown in FIG. 14.

The probe 27 of the treatment portion unit 31 is formed of a metallic material having biocompatibility (for example, a titanium alloy, etc.) as a rod-like shape. The probe 27 is integrally fixed to a case 44. The probe 27 is provided at the proximal end with an external thread portion 27A to be engaged with an internal thread portion 34A at the gripping portion 15 side.

The procedures with regard to the present embodiment will be explained below. When attaching the treatment portion unit 31 to the gripping portion 15, the treatment portion unit 31 is rotated relative to the gripping portion 15 so that the external thread portion 27A is engaged with the internal thread portion 34A. If the external thread portion 27A is completely fixed to the internal thread portion 34A, the treatment portion unit 31 is to be fixed to the gripping portion 15. However, the position of the treatment portion unit 31 relative to the gripping portion 15 is not set at a single location. Accordingly, in the present embodiment, the gripping portion 15 is detached or attached relative to the treatment portion unit 31 at a discretionary angle.

For the gripping portion 15, the detection portions 47 of the detection unit 37 are arranged around the central axis C of the vibration transmitting member 34 (probe 27). With this structure, the detection portions 47 can detect an operation of pushing the push-button 26, regardless of the position of the button supporting portion 52 and the push-button 26 of the treatment portion unit 31.

When detaching the treatment portion unit 31 from the gripping portion 15, the treatment portion unit 31 is rotated to remove the external thread portion 27A from the internal thread portion 34A. The treatment portion unit 31 can be easily detached from the gripping portion 15.

According to the present embodiment, the handpiece 12 includes a plurality of non-contact type detection portions 47 provided in the gripping portion 15 separately from the operation portion. The detection portions 47 are arranged on the entire perimeter of the gripping portion 15 around the central axis C, and one of the detection portions 47 which is closest to the operation portion is capable of detecting an operation of the operation portion. The gripping portion 15 is detachable and attachable at a discretionary angle relative to the treatment portion unit 31.

With this configuration, the detection portions 47 capable of detection on the entire perimeter can detect an operation of the operation portion even if the gripping portion 15 is attached to the treatment portion unit 31 at a discretionary angle.

[Fifth Embodiment]

A surgical treatment apparatus according to the fifth embodiment will be described with reference to FIGS. 15 and 17. A surgical treatment apparatus 11 of the fifth embodiment is different from the surgical treatment apparatus 11 of the first embodiment only in that a movable blocking member 62 is provided in a treatment portion unit 31. Accordingly, mainly those portions different from the first embodiment will be explained, and portions that are the same as the first embodiment will not be explained or shown in the drawings.

The treatment portion unit 31 includes a plurality of blocking members 62 provided corresponding to a plurality of push-buttons 26.

The configuration of a push-button 26 is the same as that of the first embodiment. The plurality of blocking members 62 are each provided to correspond to the respective push-buttons 26. As shown in FIG. 15, each of the blocking members 62 is arranged to block a through hole 63 provided in a button supporting portion 52 so as to face the push-button 26. The blocking member 62 can function as a magnetic shield, and can block the magnetic field toward a detection unit 37 from a detection subject portion 48 of the push-button 26 by blocking the through hole 63.

The blocking member 62 includes a pair of shafts 64 provided at an outer edge portion of the through hole 63 and attached to the button supporting portion 52, a pair of wall portions 65 rotatable around the respective shafts 64, and a pair of helical torsion coil springs 66 wound around the respective shafts.

The pair of wall portions 65 can rotate between a first position P1 in which the through hole 63 is blocked and a second position P2 in which the through hole 63 is opened. The wall portion 65 is formed of a ferromagnetic metal such as ferrite or austenitic stainless steel. Each of the helical torsion coil springs 66 can urge the wall portions 65 in the direction toward the first position P1 from the second position P2 (closing direction).

Next, the procedures with regard to the handpiece 12 of the present embodiment will be explained below. In the state where a user does not push the push-button 26, the pair of wall portions 65 are positioned at the first position P1. In this state, the push-button 26 is blocked by the pair of wall portions 65, and the magnetic field of a magnet that is a detection subject portion 48 is magnetically shielded to not move toward the detection unit 37 side.

If a user pushes the push-button 26, the bottom surface of the push-button 26 is brought into contact with the pair of wall portions 65, and the pair of wall portions 65 is moved from the first position P1, which is a closed position, to the second position P2, which is an open position. By this operation, the magnetic shield is released, and the magnetic field of the detection subject portion 48 reaches the detection unit 37 (detection portion 47). Accordingly, the detection unit 37 can detect a pushing operation of the push-button 26, and send an ON signal to a control circuit 22.

On the other hand, if the user removes his hand from the push-button, the push-button 26 is returned back to the original position by the action of the spring member 53. At the same time, by the action of the helical torsion coil springs 66, the wall portions 65 are returned back to the first position P1 from the second position P2, and the magnetic field from the detection subject portion 48 is magnetically shielded.

In the present embodiment, the blocking member 62 is provided between the push-button 26 and the detection unit 37, and the stroke of the push-button 26 can be shortened. As shown in FIG. 17, in the case where the blocking member 62 is not provided, the push-button 26 needs to be moved by a distance D1 so that the detection unit 37 determines whether or not to exceed the ON/OFF threshold value. On the other hand, in the case where the blocking member 62 is provided between the push-button 26 and the detection unit 37, as in the present embodiment, the blocking member 62 is closed at a point M in the middle of the stroke of the push-button 26, and then the magnetic flux density at the detection unit 37 decreases abruptly. Accordingly, in the present embodiment, the push-button 26 needs to move only by a distance D2 shorter than the distance D1. In the present embodiment, downsizing is realized by reducing the stroke of the push-button 26.

The present embodiment adopts the blocking member 62 that is placed at the first position P1 between the operation unit and the detection portion 47, and blocks the magnetic field from the detection subject portion 48 when the operation unit is away from the detection portion 47, and that can be moved to the second position P2 where the detection subject portion 48 is exposed toward the detection portion 47 when the operation portion becomes close to the detection portion 47.

According to this configuration, the magnetic field of the detection subject portion 48 positioned away from the detection portion 47 can be blocked, thereby reducing the stroke of the operation position. Thus, the handpiece 12 can be downsized, and operability for the doctor can be improved.

[Sixth Embodiment]

A surgical treatment apparatus according to the sixth embodiment will be described with reference to FIGS. 18 and 20. A surgical treatment apparatus 11 of the sixth embodiment is different from the surgical treatment apparatus 11 of the first embodiment only in that a ferromagnetic body 81 which has an essentially cylindrical shape is provided in a treatment portion unit 31.

As shown in FIG. 18, the ferromagnetic body 81 has an essentially cylindrical shape, and is arranged to enclose a detection subject portion 48 (magnet). The ferromagnetic body 81 is fixed to a base portion 52A. The ferromagnetic body 81 is formed of a metal such as ferrite or austenitic stainless steel.

The procedures with regard to the present embodiment will be explained below. In the state where a user does not push a push-button 26, the essentially cylindrical ferromagnetic body 81 acts as a magnetic shield. As a result, the magnetic field (magnetic flux density) of magnet reaching the detection unit 37 side is reduced, as indicated by the solid curve in FIG. 20.

When a user pushes the push-button 26, as shown in FIG. 19, the essentially cylindrical ferromagnetic body 81 acts as a yoke. As a result, the magnetic field (magnetic flux density) of a magnet reaching the detection unit 37 side is intensified, as indicated by the solid curve in FIG. 20.

In the present embodiment, the essentially cylindrical ferromagnetic body 81 is provided, and the stroke of the push-button 26 can be shortened. As indicated by a broken curve shown in FIG. 20, in the case where the ferromagnetic body 81 is not provided, the push-button 26 needs to be moved by a distance D1 so that the detection unit 37 determines whether or not to exceed the ON/OFF threshold value. In contrast, in the present embodiment, the push-button 26 needs to move only by a distance D2 shorter than the distance D1 if the ferromagnetic body 81 is provided, as indicated by the solid curve of FIG. 20. In the present embodiment, the stroke of the push-button 26 is shortened, and accordingly, the handpiece 12 can be downsized, and operability for the doctor can be improved.

[Modification of Sixth Embodiment]

A surgical treatment apparatus according to the modification of the sixth embodiment will be described with reference to FIG. 21. A surgical treatment apparatus 11 of the present modification is different from the surgical treatment apparatus 11 of the sixth embodiment only in that a holding portion 82 of a detection subject portion 48 of a treatment portion unit 31 is formed of a ferromagnetic body.

The holding portion 82 is formed of a ferromagnetic body. The holding portion 82 is formed of a metal such as ferrite or austenitic stainless steel. The holding portion 82 has a recess, and holds the detection subject portion 48 (magnet) within the recess.

In the present embodiment, the ferromagnetic body 81 and the holding portion 82 that is also a ferromagnetic body are provided, and the magnetic field of the detection subject portion 48 is further intensified by the effects of the yoke. Accordingly, the stroke of the push-button 26 can be further shortened. With this structure, the stroke of the push-button 26 is shortened, and accordingly, the handpiece 12 can be downsized, and operability for the doctor can be improved.

[Second Modification of Sixth Embodiment]

A surgical treatment apparatus according to the second modification of the sixth embodiment will be described with reference to FIG. 22. A surgical treatment apparatus 11 of the present modification is different from the surgical treatment apparatus 11 of the sixth embodiment only in that a detection subject portion 48 is cylindrical, and the detection subject portion 48 of the treatment portion unit 31 is fitted in an essentially cylindrical ferromagnetic body 81.

The detection subject portion 48 is cylindrical, and a support 83 formed of synthetic resin is inserted into the detection subject portion 48. The detection subject portion 48 is fitted in a hole of the essentially cylindrical ferromagnetic body 81.

The procedures with regard to the present modification will be explained below. In the state where a user does not push a push-button 26, the essentially cylindrical ferromagnetic body 81 acts as a magnetic shield. As a result, the magnetic field (magnetic flux density) of a magnet reaching the detection unit 37 side is reduced, the same as in the sixth embodiment.

When a user pushes the push-button 26, the essentially cylindrical ferromagnetic body 81 acts as a yoke. As a result, the magnetic field (magnetic flux density) of magnet reaching the detection unit 37 side is intensified, the same as in the sixth embodiment.

In the present modification, the ferromagnetic body 81 is provided, and the detection subject portion 48 is fitted in the ferromagnetic body 81. Accordingly, the stroke of the push-button 26 can be shortened. That is, similar to the case indicated by the broken curve of FIG. 20, in the case where the ferromagnetic body 81 is not provided, the push-button 26 needs to be moved by a distance D1 so that the detection unit 37 can determine whether or not to exceed the ON/OFF threshold value. In contrast, if the ferromagnetic body 81 is provided as in the present modification, the push-button 26 needs to move only by a distance D2 shorter than the distance D1, as indicated by the solid curve of FIG. 20. In the present embodiment, the stroke of the push-button 26 is shortened, and accordingly, the handpiece 12 can be downsized, and operability for the doctor can be improved.

[Seventh Embodiment]

Figure 24:
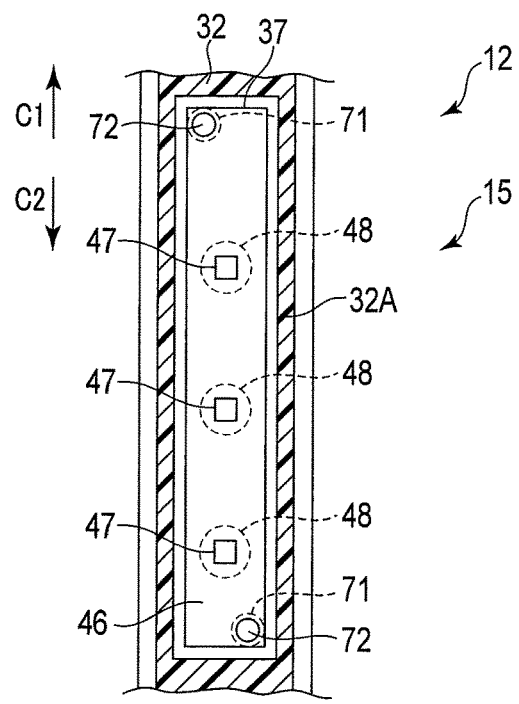
FIG. 24 is a cross-sectional view of a printed board and a storage portion of a housing of the detection unit shown in FIG. 18.

A handpiece 12 according to the seventh embodiment will be described with reference to FIGS. 23 to 24. A handpiece 12 of the seventh embodiment is different from the first embodiment only in that a positioning piece 71 is provided at the treatment portion unit 31 side, and an inducement member 72 is provided on a printed board 46 of a detection unit 37. Accordingly, mainly those portions different from the first embodiment will be explained, and portions that are the same as the first embodiment will not be explained or shown in the drawings.

The detection unit 37 of the gripping portion 15 includes a printed board 46 housed in a storage portion 32A of a housing 32, and a plurality of (three) detection portions 47 mounted on the printed board 64, and a pair of inducement members 72 provided at diagonal corners of the printed board 46. The printed board 46 can move in a direction parallel to a plane of the printed board 46 inside of the frame-like storage portion 32A. That is, a gap of approximately 0.5 mm to 2.0 mm is defined between the outer edge of the printed board 46 and a wall portion forming the storage portion 32A.

Each of the inducement members 72 is formed, for example, of a neodymium magnet. The inducement member 72 is not limited to be formed of a neodymium magnet. Other kinds of magnets such as a samarium-cobalt magnet, ferrite magnet, alnico magnet, etc. can be adopted for the inducement member 72.

The treatment portion unit 31 includes a pair of positioning pieces 71 provided in a button supporting portion 52. The configuration of the other elements is the same as that of the first embodiment.

The pair of positioning pieces 71 are attached to a surface side opposed to a probe 27 of the button supporting portion 52. Each of the pair of positioning pieces 71 is provided around a diagonal corner of the essentially square-shaped button supporting portion 52. The positioning pieces 71 are formed of a ferromagnetic metal such as ferrite or austenitic stainless steel. The positioning pieces 71 are formed close to the push-button 26 (operation portion). In the present embodiment, the inducement members 72 are formed of a magnet, and the pair of positioning pieces 71 are formed of a ferromagnetic metal. However, the inducement members 72 may be formed of a ferromagnetic metal such as ferrite or austenitic stainless steel, and the pair of positioning pieces 71 are formed of a magnet such as a neodymium magnet, a samarium-cobalt magnet, a ferrite magnet, an alnico magnet, etc.

The procedures with regard to the present embodiment will be explained below. In the present embodiment, if the treatment portion unit 31 is fixed to a gripping portion 15, the positioning pieces 71 at the treatment portion unit 31 side are opposed to the inducement members 72 at the gripping portion 15 side. In this case, the inducement members 72 are induced by the positioning pieces 71, and the printed board 46 of the detection unit 37 is correctly positioned relative to the button supporting portion 52. Accordingly, the detection portion 47 correctly faces relative to the push-button 26 (detection subject portion 48), and the detection portion 47 on the printed board 46 can accurately detect a pushing operation of the push-button 26.

In the present embodiment, the positioning pieces 71 are provided at the treatment portion unit 31 side, and the inducement members 72 are provided at the gripping portion 15 side. However, it may be possible that the inducement members 72 are provided at the treatment portion unit 31 side, and the positioning pieces 71 are provided at the gripping portion 15 side. In addition, both of the positioning pieces 71 and the inducement members 72 may be a magnet member.

According to the present embodiment, the surgical treatment apparatus 11 includes the ferromagnetic positioning pieces 71 provided close to the operation portion, the detection unit 47 is mounted along with the magnetic members 72 on the printed board 46 which is movable relative to the housing 32 of the gripping portion 15, and the magnetic members 72 are induced by the positioning pieces 71 to be positioned relative to the operation portion.

With this configuration, the detection portion 47 can be correctly positioned relative to the operation portion with a simple structure.

[Eighth Embodiment]

Figure 25:
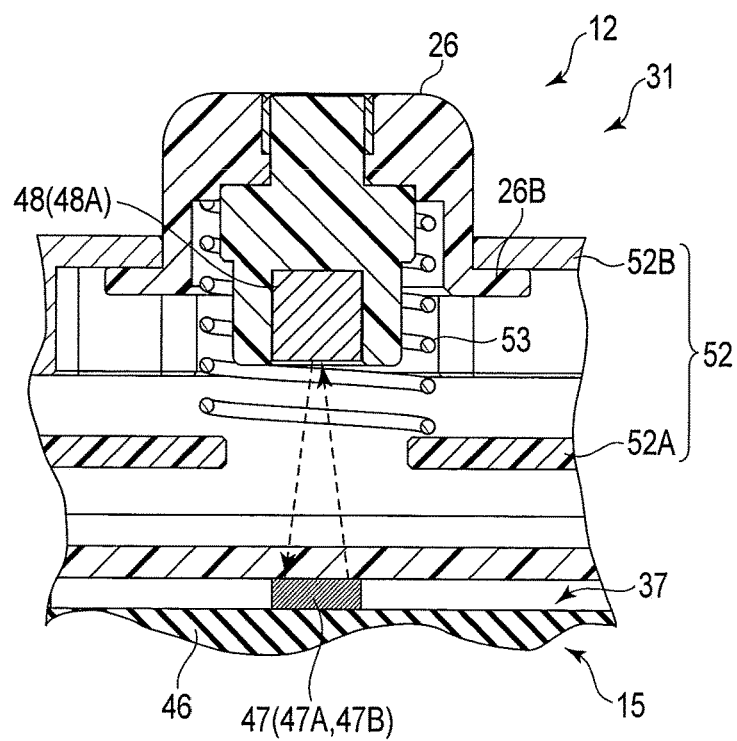
FIG. 25 is a cross-sectional view of a push-button and a detection unit of a surgical treatment apparatus according to the eighth embodiment.

A handpiece 12 according to the eighth embodiment will be described with reference to FIG. 25. A handpiece 12 of the eighth embodiment is different from the first embodiment only in that a detection portion 47 includes a transmit portion 47A and a receive portion 47B, and a detection subject portion 48 is formed of a reflective portion 48A which is capable of reflecting infrared rays. Accordingly, mainly those portions different from the first embodiment will be explained, and portions that are the same as the first embodiment will not be explained or shown in the drawings.

The detection unit 37 of the gripping portion 15 includes a printed board 46 housed in a storage portion 32A of a housing 32, and a plurality of (three) detection portions 47 mounted on the printed board 46. The printed board 46 is formed as a hard plate. In the present embodiment, the detection portion 47 is formed of an element (chip) that integrally includes the transmit portion 47A and the receive portion 47B that are capable of receiving and transmitting infrared rays. The transmit portion 47A is formed, for example, of an infrared LED. The receive portion 47B is formed, for example, of a photodiode. The receive portion 47B is not limited to be formed of a photodiode, but may be a discretionary selected element that is capable of receiving infrared rays, such as a photo transistor, a photo IC, a thermoelectron element, a pyroelectric element, etc.

A push-button 26 of a treatment portion unit 31 includes a detection subject portion 48 at the bottom part, which is to be detected by a detection unit 37 at a gripping portion 15 side. The detection subject portion 48 is formed, for example, of the reflective portion 48A (reflective plate) that is capable of reflecting infrared rays from the detection portion 47. The reflective portion 48A is formed, for example, of a resin material, the surface of which is subjected to mirror finishing. The resin material used for the reflective portion 48A is a thermoplastic resin which has a heat distortion temperature of 100° C. or less, for example.

In the present embodiment, the treatment portion unit 31 is a disposable part that is assumed to be used only once. Accordingly, the treatment portion unit 31 is devised to prevent the unit from being erroneously reused.

In the surgical treatment apparatus 11 of the present embodiment, if a user performs a high-temperature sterilization process such as autoclaving on the treatment portion unit 31, the mirror surface of the reflective portion 48A is coarsely deformed by thermal deformation. Thus, infrared rays transmitted from the transmit portion 47A are diffused on the surface of the reflective portion 48A, and cannot be received at the receive portion 47B. Accordingly, even if the treatment portion unit 31 subjected to autoclaving or the like is attached to the gripping portion 15, and a doctor operates the push-button 26, the operation of the push-button 26 is not detected by the detection unit 37. With this structure, the treatment portion unit 31 is prevented from being reused.

Next, the procedure when the push-button 26 of the present embodiment is operated will be described with reference to FIG. 25. In a state where a doctor has not pushed the push-button 26, the detection portion 47 (receive portion 47B) of the detection unit 37 detects that the distance to the detection subject portion 48 is equal to or greater than a threshold, and sends an OFF signal to a control circuit of a driving device 13.

When the doctor pushes the push-button 26, the detection portion 47 (receive portion 47B) of the detection unit 37 detects that the distance to the detection subject portion 48 is equal to or less than a threshold (the magnetic flux density at the detection portion 47 is equal to or greater than the threshold) and sends an ON signal to the control circuit 22 of the driving device 13. The control circuit 22 performs the processing corresponding to the ON signal (transmitting a signal to a high-frequency current supply circuit 21, and supplying a high-frequency current corresponding to an incision mode from the high-frequency current supply circuit 21).

When the doctor removes his finger from the push-button 26, the detection portion 47 (receive portion 47B) of the detection unit 37 detects that the distance to the detection subject portion 48 becomes equal to or greater than the threshold (the magnetic flux density at the detection portion 47 is equal to or less than the threshold), and sends an OFF signal to the control circuit 22 of the driving device 13. By this processing, supply of a high-frequency current to the probe 27 is stopped.

According to the present embodiment, the non-contact type detection portion 47 can be formed of the transmit portion 47A and the receive portion 47B that are capable of transmitting or receiving infrared rays. Thus, it is possible to reduce the operation force of the operation portion with the simple structure, in the similar manner to the above embodiments, and the treatment portion unit 31 can omit a switch substrate or an electric contact for a switch, thereby downsizing the treatment portion unit 31 and reducing the manufacturing costs for the treatment portion unit 31.

The present invention is not limited to the above-described embodiments, and can be modified in various manners when reduced to practice, without departing from the gist of the invention. That is, the above embodiments merely show an example, and the other types of non-contact type sensors such as a non-contact type sensor capable of sensing light, electromagnetic waves, a laser, etc. can be used for the detection portion 47 and the detection subject portion 48. In addition, it is also possible to form a surgical treatment apparatus 11 by combining the surgical treatment apparatuses 11 described in each of the embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical treatment apparatus comprising:
   a treatment portion unit including a treatment portion that performs treatment on a living tissue;
   at least one operation portion provided in the treatment portion unit, the at least one operation portion being a pushable member that is movable in a radial direction relative to a central axis of the treatment portion unit between an unpressed position and a pressed position in response to an operation of an operator;
   a detection subject portion provided in the at least one operation portion;
   a gripping portion provided separately from the treatment portion unit, the gripping portion being detachable and attachable relative to the treatment portion unit;
   a non-contact type detection portion provided in the gripping portion and separated from the at least one operation portion, the detection portion being configured to detect an operation of the detection subject portion in accordance with whether the at least one operation portion is in the unpressed position or the pressed position;
   an energy supply portion provided within the gripping portion, the energy supply portion supplying energy to the treatment portion; and
   a driving device connected to the gripping portion, the driving device supplying energy to the energy supply portion in accordance with a detection result of the detection portion,
   wherein the detection portion is positioned to face the detection subject portion in the radial direction relative to the central axis of the treatment portion unit so that, when the treatment portion unit is attached to the gripping portion, the detection subject portion is within a range of being able to be detected by the detection portion.

2. The surgical treatment apparatus according to claim 1, wherein:
   the energy supply portion includes an ultrasonic transducer that is capable of generating ultrasonic vibration,
   the treatment portion is a probe to which the ultrasonic vibration is transmitted, and
   the driving device includes an ultrasonic transducer driving portion that drives the ultrasonic transducer.

3. The surgical treatment apparatus according to claim 1, wherein:
   the treatment portion is a probe that is capable of supplying a high-frequency current, and
   the driving device includes a high-frequency current driving portion that supplies a high-frequency current to the probe through the energy supply portion.

4. The surgical treatment apparatus according to claim 1, further comprising an attachment detection portion provided in the gripping portion, the attachment detection portion being capable of detecting that the treatment portion unit is attached to the gripping portion.

5. The surgical treatment apparatus according to claim 1, wherein the detection subject portion is configured to change a property so that the detection subject portion is undetectable by the detection portion if the treatment portion unit is subjected to a high-temperature sterilization process.

6. The surgical treatment apparatus according to claim 1, wherein the detection subject portion is a magnet, and the detection portion is a magnetic detection element.

7. The surgical treatment apparatus according to claim 6, wherein the detection portion is capable of sensing an operation of the at least one operation portion on an entire perimeter of the gripping portion in a rotation direction.

8. The surgical treatment apparatus according to claim 6, wherein the treatment portion unit is provided with a blocking member that is movable from a first position that is between the operation unit and the detection portion so that the blocking member blocks a magnetic field from the detection subject portion when the operation unit is away from the detection portion, to a second position such that the detection subject portion is exposed toward the detection portion when the at least one operation portion comes close to the detection portion.

9. The surgical treatment apparatus according to claim 1, further comprising a second treatment portion unit that is detachable and attachable relative to the gripping portion so that, in place of the treatment portion unit, the second treatment portion unit includes a second treatment portion that performs treatment on a living tissue and at least one second operation portion that is movable in a radial direction relative to a central axis of the second treatment portion unit between an unpressed position and a pressed position in response to an operation of an operator,
wherein the at least one second operation portion of the second treatment portion unit is different from the at least one operation portion of the treatment portion unit in number, shape, and arrangement, and the second treatment portion of the second treatment portion unit is different from the treatment portion of the treatment portion unit in length and shape.

10. The surgical treatment apparatus according to claim 1, wherein:
the treatment portion unit includes a positioning piece formed of a ferromagnetic body or a magnet in a vicinity of the at least one operation portion, and
the detection portion is mounted on a printed board that is movable relative to a housing of the gripping portion together with an inducement member formed of a magnet, and the detection portion is positioned relative to the at least one operation portion when the inducement member is induced to the positioning piece.

11. The surgical treatment apparatus according to claim 1, wherein:
the treatment portion unit includes a positioning piece formed of a magnet in a vicinity of the at least one operation portion, and
the detection portion is mounted on a printed board that is movable relative to a housing of the gripping portion together with an inducement member formed of a ferromagnetic body, and the detection portion is positioned relative to the at least one operation portion when the inducement member is induced to the positioning piece.

12. The surgical treatment apparatus according to claim 1, further comprising an attachment/detachment mechanism that is configured to move the detection subject portion within a range of being detectable by the detection portion, when the treatment portion unit is attached to the gripping portion.

13. The surgical treatment apparatus according to claim 12, wherein the treatment portion is rotatable relative to the treatment portion unit around a longitudinal axis of the treatment portion.

14. The surgical treatment apparatus according to claim 1, wherein:
the detection subject portion is a magnet, and
the detection portion is capable of detecting an operation of the at least one operation portion based on whether a strength of a magnet field to be detected exceeds a threshold or falls below the threshold.

15. The surgical treatment apparatus according to claim 1, further comprising a spring member provided in the treatment portion and that is elastic relative to the central axis,
wherein the detection portion is positioned to face the detection subject portion when the treatment portion is brought into contact with a vibration transmitting member by an urging force of the spring member.

16. The surgical treatment apparatus according to claim 1, further comprising:
a receiving portion provided in the gripping portion; and
a spring member provided in the treatment portion and that is elastic relative to the central axis,
wherein the detection portion is positioned to face the detection subject portion when the treatment portion is brought into contact with a vibration transmitting member by an urging force of the spring member while the treatment portion unit is rotated by means of the receiving portion relative to the gripping portion.

17. A handpiece comprising:
a treatment portion unit including a treatment portion that performs treatment on a living tissue;
at least one operation portion provided in the treatment portion unit, the at least one operation portion being a pushable member that is movable in a radial direction relative to a central axis of the treatment portion unit between an unpressed position and a pressed position in response to an operation of an operator;
a detection subject portion provided in the at least one operation portion;
a gripping portion provided separately from the treatment portion unit, the gripping portion being detachable and attachable relative to the treatment portion unit;
a non-contact type detection portion provided in the gripping portion and separated from the at least one operation portion, the detection portion being configured to detect an operation of the detection subject portion in accordance with whether the at least one operation portion is in the unpressed position or the pressed position; and
an energy supply portion provided within the gripping portion, the energy supply portion supplying energy to the treatment portion,
wherein:
in accordance with a detection result of the detection portion, energy is supplied to the energy supply portion from a driving device connected to the gripping portion, and
the detection portion is positioned to face the detection subject portion in the radial direction relative to the central axis of the treatment portion unit so that, when the treatment portion unit is attached to the gripping portion, the detection subject portion is within a range of being able to be detected by the detection portion.

* * * * *